US012708760B2

(12) United States Patent
Green

(10) Patent No.: US 12,708,760 B2
(45) Date of Patent: Aug. 18, 2026

(54) PERCUTANEOUS HEART PUMP DISTAL SEAL

(71) Applicant: TC1 LLC, St. Paul, MN (US)

(72) Inventor: Michael L. Green, Pleasanton, CA (US)

(73) Assignee: TC1 LLC, St. Paul, MN (US)

( * ) Notice: Subject to any disclaimer, the term of this patent is extended or adjusted under 35 U.S.C. 154(b) by 503 days.

(21) Appl. No.: 18/065,822

(22) Filed: Dec. 14, 2022

(65) Prior Publication Data

US 2023/0191107 A1 Jun. 22, 2023

Related U.S. Application Data

(60) Provisional application No. 63/290,430, filed on Dec. 16, 2021.

(51) Int. Cl.

| | |
|---|---|
| ***A61M 60/414*** | (2021.01) |
| ***A61M 60/13*** | (2021.01) |
| ***A61M 60/232*** | (2021.01) |
| ***A61M 60/237*** | (2021.01) |
| ***A61M 60/804*** | (2021.01) |
| ***A61M 60/829*** | (2021.01) |

(52) U.S. Cl.

CPC .......... *A61M 60/414* (2021.01); *A61M 60/13* (2021.01); *A61M 60/237* (2021.01); *A61M 60/804* (2021.01); *A61M 60/829* (2021.01); *A61M 60/232* (2021.01)

(58) Field of Classification Search

CPC .............. A61M 60/414; A61M 60/804; A61M 60/237; A61M 60/829; A61M 60/13; A61M 60/232

See application file for complete search history.

(56) References Cited

U.S. PATENT DOCUMENTS

| | | | |
|---|---|---|---|
| 4,143,853 A | 3/1979 | Abramson | |
| 4,625,712 A | 12/1986 | Wampler | |
| 4,673,393 A | 6/1987 | Suzuki et al. | |
| 4,686,982 A | 8/1987 | Nash | |
| 4,704,121 A * | 11/1987 | Moise .................. | F04D 29/108 623/3.15 |
| 4,747,406 A | 5/1988 | Nash | |
| 4,798,594 A | 1/1989 | Hillstead | |
| 4,846,152 A | 7/1989 | Wampler et al. | |
| 4,895,557 A | 1/1990 | Moise | |
| 4,936,831 A | 6/1990 | Jaehrling et al. | |
| 4,944,722 A | 7/1990 | Carriker | |
| 5,541,167 A | 7/1996 | Hsu et al. | |
| 5,634,894 A | 6/1997 | Magram | |

(Continued)

FOREIGN PATENT DOCUMENTS

| | | |
|---|---|---|
| CN | 206443963 U | 8/2017 |
| CN | 216908915 U | 7/2022 |

(Continued)

*Primary Examiner* — Lindsey G Wehrheim

(74) *Attorney, Agent, or Firm* — WORKMAN NYDEGGER

(57) ABSTRACT

The present application describes various features for a catheter pump that prevents or inhibits unwanted fluids from entering a cavity or opening of a catheter pump. If unwanted fluids enter a cavity or opening of the catheter pump, the examples described herein cause the unwanted fluid to be expelled from the catheter pump.

22 Claims, 24 Drawing Sheets

(56) References Cited

U.S. PATENT DOCUMENTS 5,964,694 A 10/1999 Siess et al.
6,007,478 A 12/1999 Siess et al.
6,063,057 A 5/2000 Choh
6,176,848 B1 1/2001 Rau
6,544,216 B1 4/2003 Sammler
6,699,221 B2 3/2004 Vaillancourt
6,926,662 B1 8/2005 Aboul-Hosn
7,011,620 B1 3/2006 Siess
7,022,100 B1 4/2006 Aboul-Hosn
7,070,555 B2 7/2006 Siess
7,393,181 B2 7/2008 McBride
7,841,976 B2 11/2010 McBride
7,998,054 B2 8/2011 Bolling
8,157,719 B1 4/2012 Ainsworth
8,286,657 B2 10/2012 Belley et al.
8,376,707 B2 2/2013 McBride
8,489,190 B2 7/2013 Pfeffer
8,597,170 B2 12/2013 Walters
8,721,517 B2 5/2014 Zeng
9,358,329 B2 6/2016 Fitzgerald et al.
9,381,288 B2 7/2016 Schenck et al.
9,446,179 B2 9/2016 Keenan et al.
9,675,738 B2 6/2017 Tanner et al.
9,675,739 B2 6/2017 Tanner et al.
9,770,543 B2 9/2017 Tanner et al.
9,872,947 B2 1/2018 Keenan et al.
9,878,079 B2 1/2018 Pfeffer et al.
10,327,808 B2 6/2019 Blumenkranz et al.
10,449,279 B2 10/2019 Muller
10,632,241 B2 4/2020 Schenck et al.
10,668,195 B2 6/2020 Flores
10,874,783 B2 12/2020 Pfeffer et al.
11,033,728 B2 6/2021 Schenck et al.
11,033,729 B2 6/2021 Scheckel et al.
11,160,970 B2 11/2021 Muller et al.
11,666,748 B2 6/2023 Kronstedt et al.
2004/0097900 A1 5/2004 Keren et al.
2005/0090883 A1 4/2005 Westlund et al.
2005/0113631 A1 5/2005 Bolling
2006/0161095 A1 7/2006 Aboul-Hosn et al.
2008/0294112 A1 11/2008 Judson et al.
2009/0163864 A1 6/2009 Breznock et al.
2011/0004046 A1 1/2011 Campbell
2011/0295345 A1 12/2011 Wells
2012/0004495 A1 1/2012 Bolling
2012/0172655 A1 7/2012 Campbell
2012/0178985 A1 7/2012 Walters
2012/0178986 A1 7/2012 Campbell
2012/0203056 A1 8/2012 Corbett
2013/0245534 A1 9/2013 Miller et al.
2013/0303830 A1 11/2013 Zeng
2013/0303969 A1 11/2013 Keenan
2013/0303970 A1 11/2013 Keenan
2014/0010686 A1 1/2014 Tanner
2014/0012065 A1 1/2014 Fitzgerald
2014/0031606 A1 1/2014 Hansen
2014/0275725 A1 9/2014 Schenck
2016/0051806 A1 2/2016 Goldsmith
2016/0213825 A1 7/2016 Tanner
2016/0213826 A1 7/2016 Tanner
2016/0213827 A1 7/2016 Tanner
2018/0021494 A1 1/2018 Muller
2018/0256797 A1 9/2018 Schenck et al.
2019/0105437 A1 4/2019 Siess et al.
2019/0381223 A1 12/2019 Culbert et al.
2020/0023110 A1 1/2020 Jahangir
2020/0061307 A1 2/2020 Mao et al.
2020/0268951 A1 8/2020 Nitzan et al.
2020/0276369 A1 9/2020 Nitzan et al.
2020/0345979 A1 11/2020 Loh et al.
2021/0060224 A1 3/2021 Kronstedt et al.
2021/0077675 A1 3/2021 Tanner et al.
2021/0077678 A1 3/2021 Muller et al.
2021/0170081 A1 6/2021 Kanz
2021/0236796 A1 8/2021 Dahlgren et al.
2022/0018445 A1 1/2022 Kung et al.
2022/0161021 A1 5/2022 Mitze et al.
2023/0096277 A1 3/2023 Van et al.
2023/0149669 A1 5/2023 Butler et al.
2023/0181893 A1 6/2023 Su et al.
2023/0201530 A1 6/2023 Goral et al.

FOREIGN PATENT DOCUMENTS

CN 115459507 A 12/2022
JP 3694031 B2 9/2005
WO 2005/046779 A2 5/2005
WO 2023/014742 A1 2/2023

* cited by examiner 317B
300
317A
335
3
301
120A
101
317
335
1
302
16

8
71
355
3A
308
13
358
16
3B
303
309
307
304
311B
311A
301
305
306

PERCUTANEOUS HEART PUMP DISTAL SEAL

CROSS-REFERENCE TO RELATED APPLICATIONS

This application claims the benefit of priority to U.S. Provisional Patent Application No. 63/290,430, titled PHP Distal Seal, filed on Dec. 16, 2021, the entire contents of which are hereby incorporated herein by reference.

TECHNICAL FIELD

This application is directed to catheter pumps for mechanical circulatory support of a heart.

BACKGROUND OF THE INVENTION

Heart disease is a major health problem that has a high mortality rate. Physicians increasingly use mechanical circulatory support systems for treating heart failure. The treatment of acute heart failure requires a device that can provide support to the patient quickly. Physicians desire treatment options that can be deployed quickly and are minimally-invasively.

Mechanical circulatory support (MCS) systems and ventricular assist devices (VADs) have gained greater acceptance for the treatment of acute heart failure such as acute myocardial infarction (MI) or to support a patient during high risk percutaneous coronary intervention (PCI). An example of an MCS system is a rotary blood pump placed percutaneously, e.g., via a catheter.

In a conventional approach, a blood pump is inserted into the body and connected to the cardiovascular system, for example, to the left ventricle and the ascending aorta to assist the pumping function of the heart. Other known applications include placing the pump in the descending aorta, a peripheral artery, and the like. Typically, acute circulatory support devices are used to reduce the afterload on the heart muscle and provide blood flow for a period of time to stabilize the patient prior to heart transplant or for continuing support.

There is a need for improved mechanical circulatory support devices for treating acute heart failure. There is a need for minimally-invasive devices designed to provide near full heart flow rate.

There is a need for a blood pump with improved performance and clinical outcomes. There is a need for a pump that can provide elevated flow rates with reduced risk of hemolysis and thrombosis. There is a need for a pump that can be inserted minimally-invasively and provide sufficient flow rates for various indications while reducing the risk of major adverse events.

There is a need for a heart pump that can be placed minimally-invasively, for example, through an 18FR, 14FR, or 8FR incision. In one aspect, there is a need for a heart pump that can provide an average flow rate of 4 Lpm or more during operation, for example, at 62 mmHg of aortic pressure.

While the flow rate of a rotary blood pump can be increased by rotating the impeller faster, higher rotational speeds are known to increase the risk of hemolysis, which can lead to adverse outcomes and in some cases death. Higher speeds also lead to performance and patient comfort challenges. Many percutaneous ventricular assist devices (VADs) have driveshafts between the motor and impeller rotating at high speeds. Some percutaneous VADs are designed to rotate at speeds of more than 15,000 RPM, and in some cases more than 25,000 RPM in operation. The vibration, noise, and heat from the motor and driveshaft can cause discomfort to the patient, especially when positioned inside the body. Moreover, fluids (such as saline and/or blood) may enter the motor or other portion of the catheter pump, which can damage the motor and/or impair operation of the catheter pump. Accordingly, there is a need for a device that prevents unwanted fluids from entering portions of the catheter pump and also expels the unwanted fluids from the catheter pump thereby improving performance.

These and other problems may be overcome by the embodiments described herein.

SUMMARY

In one aspect the present disclosure describes a catheter pump system. In an example, the catheter pump system includes an impeller comprising an impeller tip. The impeller tip is provided on a distal end of the impeller. The impeller tip defines an inner volume. The impeller tip also includes a feature. In an example, the feature defines an opening extending from an outer surface of the impeller tip to the inner volume. Movement of the impeller tip expels fluid through the feature from within the inner volume through the opening to prevent the fluid from entering a portion of the catheter pump system.

Also described is a catheter pump system, comprising an impeller, an impeller tip and an impeller shaft. The impeller tip is disposed on a distal end of the impeller. In an example, the impeller tip defines an inner volume and a plurality of features. Each of the plurality of features define a channel between the inner volume and a surface portion of the impeller tip. The impeller shaft is coupled to the impeller. In an example, the impeller shaft defines one or more grooves arranged in a helical manner. Each of the one or more grooves and each of the plurality of features expel a fluid from respective portions of the catheter pump system in response to a movement of the impeller.

The present disclosure also describes a method for operating a catheter pump system. In an example, the method includes causing movement of an impeller of the catheter pump system. In response to the movement, a fluid is expelled from an inner volume defined by an impeller tip associated with the impeller. In an example, the fluid is expelled from the inner volume via a plurality of features, each of the plurality of features includes a channel that extends from the inner volume to an outer surface of the impeller tip.

BRIEF DESCRIPTION OF THE DRAWINGS

A more complete appreciation of the subject matter of this application and the various advantages thereof can be realized by reference to the following detailed description, in which reference is made to the accompanying drawings in which.

More detailed descriptions of various embodiments of components for heart pumps useful to treat patients experiencing cardiac stress, including acute heart failure, are set forth below.

DETAILED DESCRIPTION

This application is generally directed to apparatuses for inducing motion of a fluid relative to the apparatus. Exemplars of circulatory support systems for treating heart failure, and in particular emergent and/or acute heart failure, are disclosed in U.S. Pat. Nos. 4,625,712; 4,686,982; 4,747,406; 4,895,557; 4,944,722; 6,176,848; 6,926,662; 7,022,100; 7,393,181; 7,841,976; 8,157,719; 8,489,190; 8,597,170; 8,721,517 and U.S. Pub. Nos. 2012/0178986 and 2014/0010686, the entire contents of which patents and publications are incorporated herein by reference for all purposes. In addition, this application incorporates by reference in its entirety and for all purposes the subject matter disclosed in each of the following applications and the provisional applications to which they claim priority: application Ser. No. 15/654,402, entitled "FLUID SEALS FOR CATHETER PUMP MOTOR ASSEMBLY," filed on Jul. 19, 2017, and claiming priority to U.S. Provisional Application No. 62/365,215; application Ser. No. 15/003,576, entitled "REDUCED ROTATIONAL MASS MOTOR ASSEMBLY FOR CATHETER PUMP," filed on Jan. 21, 2016, and claiming priority to U.S. Provisional Patent Application No. 62/106,670; application Ser. No. 15/003,682, entitled "MOTOR ASSEMBLY WITH HEAT EXCHANGER FOR CATHETER PUMP," filed on Jan. 21, 2016, and claiming priority to U.S. Provisional Patent Application No. 62/106,675; and application Ser. No. 15/003,696, entitled "ATTACHMENT MECHANISMS FOR MOTOR OF CATHETER PUMP," filed on Jan. 21, 2016, and claiming priority to U.S. Provisional Patent Application No. 62/106,673.

The present application describes various features for a catheter pump that prevents or inhibits unwanted fluids from entering a cavity or opening of a catheter pump. If unwanted fluids were to enter a cavity or opening of the catheter pump, the examples described herein enable the unwanted fluid to be expelled from the catheter pump. Some embodiments generally relate to various configurations for a motor assembly adapted to drive an impeller at a distal end of a catheter pump, e.g., a percutaneous heart pump. The motor described herein may be used for other applications including catheter-based devices like an atherectomy device. In such applications, the disclosed motor assembly is disposed outside the patient in some embodiments. In other embodiments, the disclosed motor assembly and/or features of the motor are miniaturized and sized to be inserted within the body, e.g., within the vasculature.

Figure 1A:
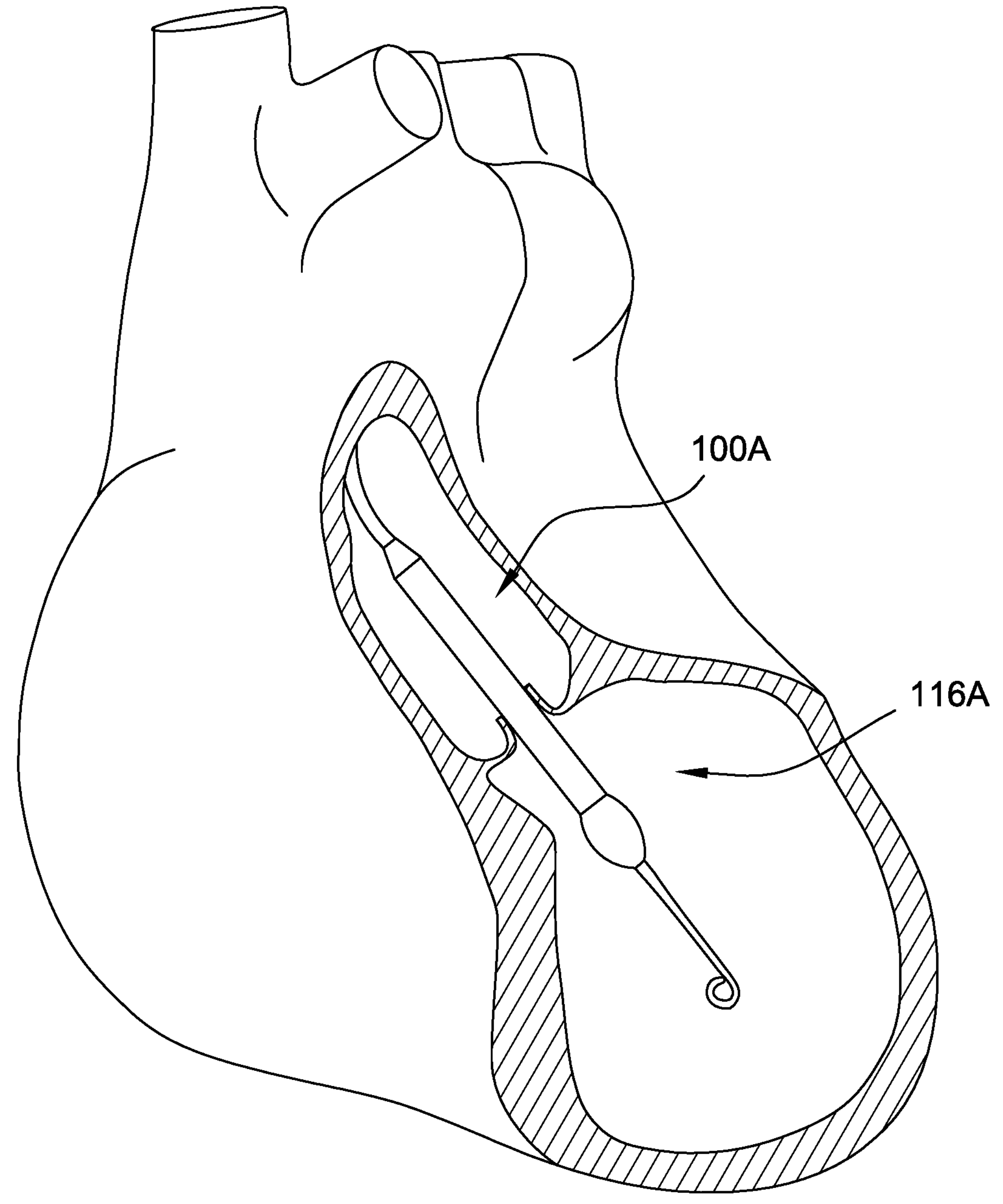
FIG. 1A illustrates an embodiment of a catheter pump system with an impeller assembly configured for percutaneous application and operation.
Figure 1B:
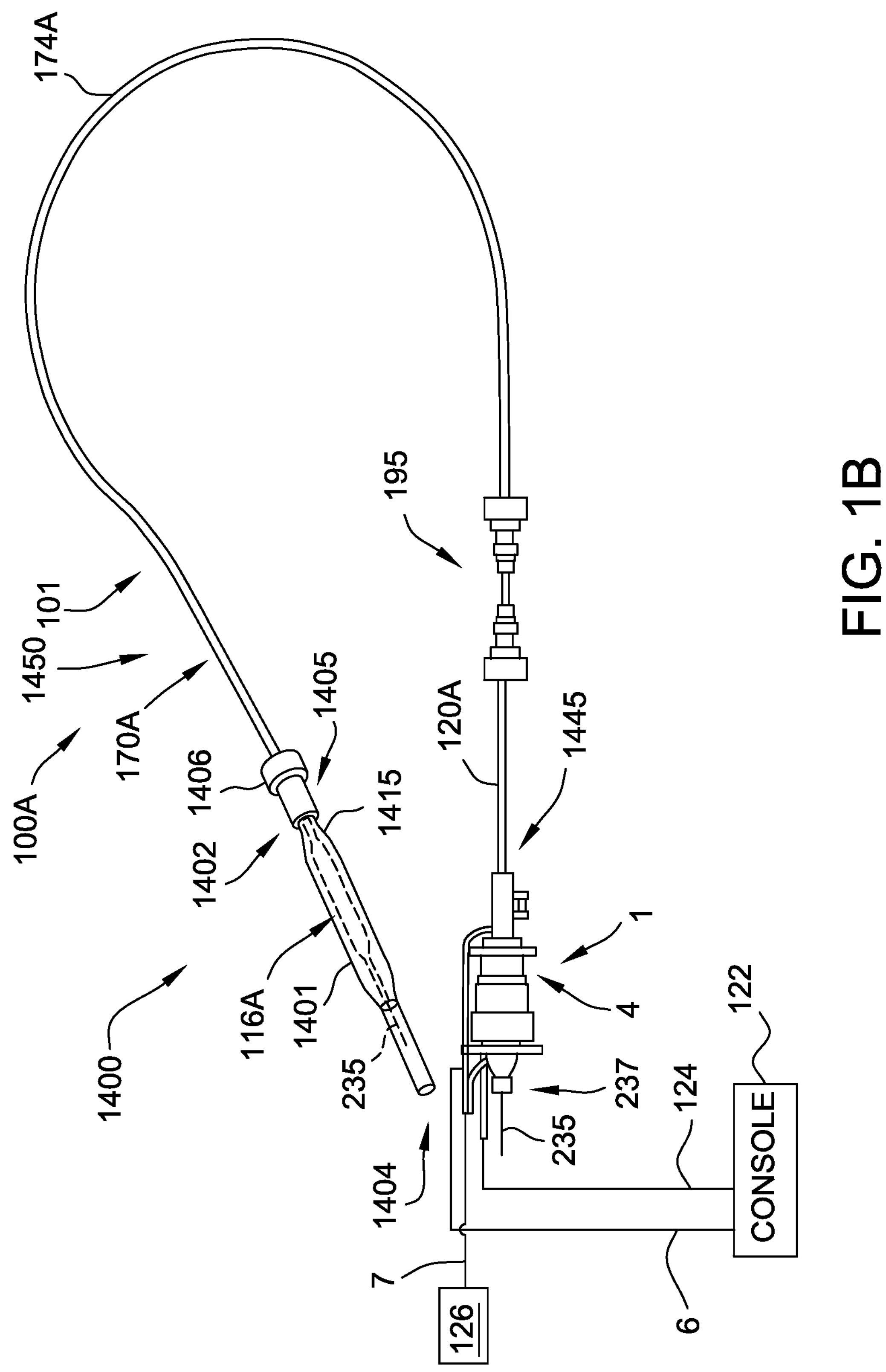
FIG. 1B is a schematic view of an embodiment of a catheter pump system adapted to be used in the manner illustrated in FIG. 1A.

FIGS. 1A-1B show aspects of an exemplary catheter pump 100A that can provide relatively high blood flow rates (i.e. full or near full blood flow). As shown in FIG. 1B, the pump 100A includes a motor assembly 1 driven by a console 122, which can include an electronic controller and various fluid handling systems. The console 122 directs the operation of the motor assembly 1 and an infusion system that supplies a flow of fluid in the pump 100A. Additional details regarding the exemplary console 122 may be understood from U.S. Patent Publication No. US 2014/0275725, the contents of which are incorporated by reference herein in their entirety and for all purposes.

The pump 100A includes a catheter assembly 101 that can be coupled with the motor assembly 1 and can house an impeller in an impeller assembly 116A within a distal portion of the catheter assembly 101 of the pump 100A. In various embodiments, the impeller is rotated remotely by the motor assembly 1 when the pump 100A is operating. For example, the motor assembly 1 can be disposed outside the patient. In some embodiments, the motor assembly 1 is separate from the console 122, e.g., to be placed closer to the patient. In the exemplary system the pump is placed in the patient in a sterile environment and the console is outside the sterile environment. In one embodiment, the motor is disposed on the sterile side of the system. In other embodiments, the motor assembly 1 is part of the console 122.

Figure 1C:
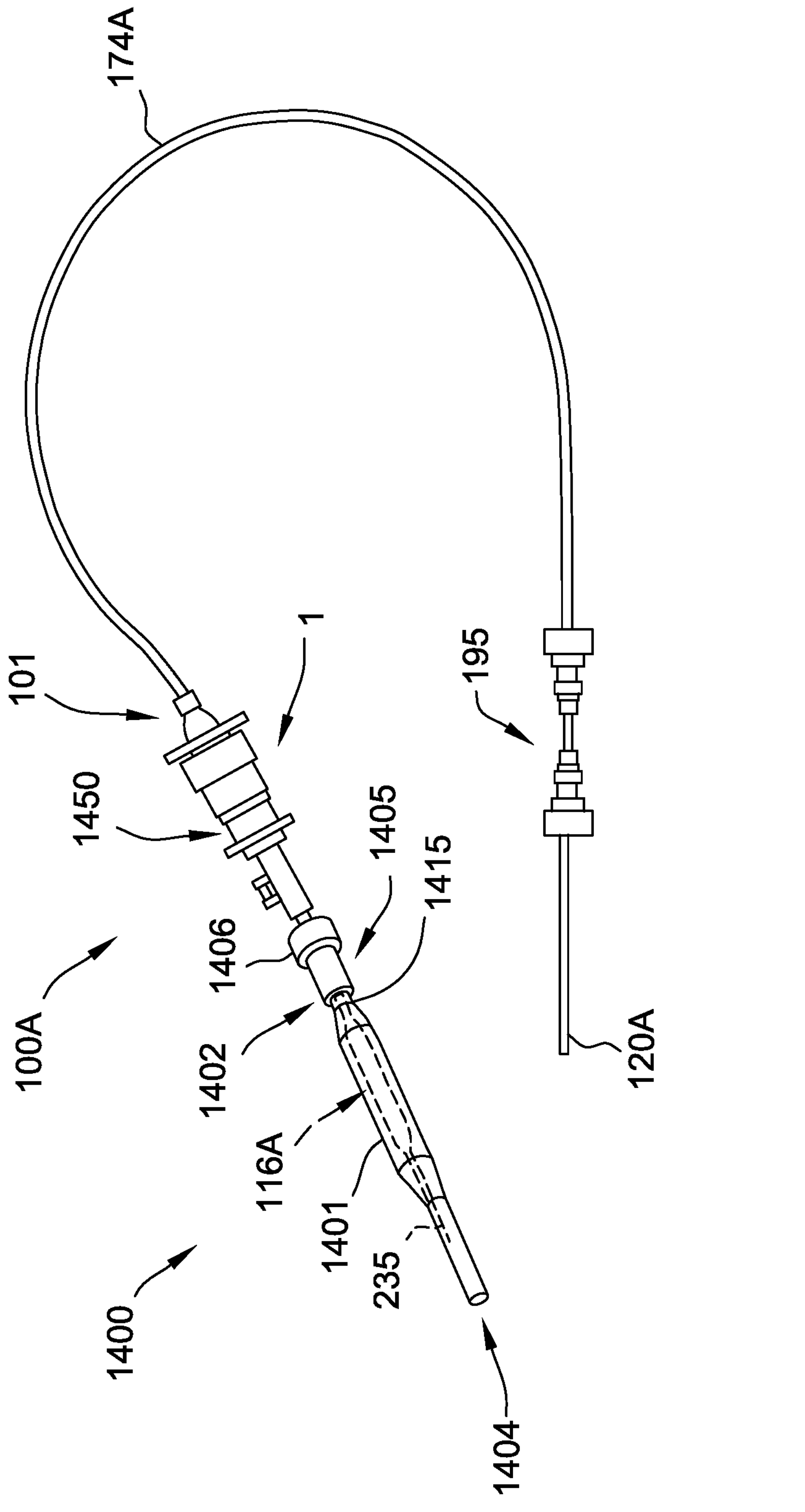
FIG. 1C is a schematic view of another embodiment of a catheter pump system.

In still other embodiments, the motor assembly 1 is miniaturized to be insertable into the patient. For example, FIG. 1C is a schematic view of another embodiment of a catheter pump system. FIG. 1C is similar to FIG. 1B, except the motor assembly 1 is miniaturized for insertion into the body. As shown in FIG. 1C, for example, the motor assembly 1 can be disposed proximal the impeller assembly 116A. The motor assembly 1 can be generally similar to the motor assembly shown in FIG. 2, except the motor assembly 1 is sized and shaped to be inserted into the patient's vasculature. One or more electrical lines may extend from the motor to the console outside the patient. The electrical lines can send signals for controlling the operation of the motor. Such embodiments allow a drive shaft coupled with the impeller and disposed within the catheter assembly 101 to be much shorter, e.g., shorter than the distance from the aortic valve to the aortic arch (about 5 cm or less). Various embodiments of the motor assembly 1 are disclosed herein, including embodiments having a rotor disposed within a stator assembly. In various embodiments, waste fluid can pass through a housing in which the rotor is disposed to help cool the motor assembly 1. In some embodiments, the housing in which the motor assembly 1 of FIG. 1C is disposed can be sealed from fluids (e.g., blood and/or saline) so as to isolate the electrical lines from the fluids. For example, as disclosed in the embodiments of FIGS. 8A-9B, one or more seals can be provided to impede or prevent the flow of liquids into the housing.

FIG. 1A illustrates one use of the catheter pump 100A. A distal portion of the pump 100A including a catheter assembly including the impeller assembly 116A is placed in the left ventricle (LV) of the heart to pump blood from the LV into the aorta. The pump 100A can be used in this way to treat a wide range of heart failure patient populations including, but not limited to, cardiogenic shock (such as acute myocardial infarction, acute decompensated heart failure, or postcardiotomy), myocarditis, and others. The pump can also be used for various other indications including to support a patient during a cardiac invention such as a high-risk percutaneous coronary intervention (PCI) or ablation. One convenient manner of placement of the distal portion of the pump 100A in the heart is by percutaneous access and delivery using a modified Seldinger technique or other methods familiar to cardiologists. These approaches enable the pump 100A to be used in emergency medicine, a catheter lab and in other medical settings. Modifications can also enable the pump 100A to support the right side of the heart. Example modifications that could be used for right side support include providing delivery features and/or shaping a distal portion that is to be placed through at least one heart valve from the venous side, such as is discussed in U.S. Pat. Nos. 6,544,216; 7,070,555; and US 2012-0203056A1, all of which are hereby incorporated by reference herein in their entirety for all purposes.

The impeller assembly 116A (e.g., the impeller and cannula) can be expandable and collapsible. In the collapsed state, the distal end of the catheter pump 100A can be advanced to the heart, for example, through an artery. In the expanded state the impeller assembly 116A is able to pump blood at relatively high flow rates. In particular, the expandable cannula and impeller configuration allows for decoupling of the insertion size and flow rate, in other words, it allows for higher flow rates than would be possible through a lumen limited to the insertion size with all other things being equal. In FIGS. 1A and 1B, the impeller assembly 116A is illustrated in the expanded state. The collapsed state can be provided by advancing a distal end 170A of an elongate body 174A distally over the impeller assembly 116A to cause the impeller assembly 116A to collapse. This provides an outer profile throughout the catheter assembly and catheter pump 100A that is of small diameter during insertion, for example, to a catheter size of about 12.5 FR in various arrangements. In other embodiments, the impeller assembly 116A is not expandable.

The mechanical components rotatably supporting the impeller within the impeller assembly 116A permit relatively high rotational speeds while controlling heat and particle generation that can come with high speeds. The infusion system delivers a cooling and lubricating solution to the proximal end 1506 (see FIG. 1D) of the catheter pump 100A for these purposes. The space for delivery of this fluid is extremely limited. Some of the space is also used for return of the fluid as waste fluid. Providing secure connection and reliable routing of fluid into and out of the catheter pump 100A is critical and challenging in view of the small profile of the catheter assembly 101.

When activated, the catheter pump 100A can effectively support, restore and/or increase the flow of blood out of the heart and through the patient's vascular system. In various embodiments disclosed herein, the pump 100A can be configured to produce a maximum flow rate (e.g. zero mm Hg backpressure) of greater than 4 Lpm, greater than 4.5 Lpm, greater than 5 Lpm, greater than 5.5 Lpm, greater than 6 Lpm, greater than 6.5 Lpm, greater than 7 Lpm, greater than 7.5 Lpm, greater than 8 Lpm, greater than 9 Lpm, or greater than 10 Lpm. In various embodiments, the pump 100A can be configured to produce an average flow rate at 62 mmHg of greater than 2 Lpm, greater than 2.5 Lpm, greater than 3 Lpm, greater than 3.5 Lpm, greater than 4 Lpm, greater than 4.25 Lpm, greater than 4.5 Lpm, greater than 5 Lpm, greater than 5.5 Lpm, greater than 6 Lpm, greater than 6.5 Lpm, greater than 7 Lpm, greater than 8 Lpm, or greater than 9 Lpm.

Various aspects of the pump and associated components can be combined with or substituted for those disclosed in U.S. Pat. Nos. 7,393,181; 8,376,707; 7,841,976; 7,022,100; and 7,998,054, and in U.S. Pub. Nos. 2011/0004046; 2012/0178986; 2012/0172655; 2012/0178985; and 2012/0004495, the entire contents of each of which are incorporated herein for all purposes by reference. In addition, various aspects of the pump and system can be combined with those disclosed in U.S. Patent Publication No. US 2013/0303970, entitled "DISTAL BEARING SUPPORT," filed on Mar. 13, 2013; U.S. Patent Publication No. US 2014/0275725, entitled "FLUID HANDLING SYSTEM," filed on Mar. 11, 2014; U.S. Patent Publication No. US 2013/0303969, entitled "SHEATH SYSTEM FOR CATHETER PUMP," filed on Mar. 13, 2013; U.S. Patent Publication No. US 2013/0303830, entitled "IMPELLER FOR CATHETER PUMP," filed on Mar. 13, 2013; U.S. Patent Publication No. US 2014/0012065, entitled "CATHETER PUMP," filed on Mar. 13, 2013; and U.S. Patent Publication No. US 2014/0010686, entitled "MOTOR ASSEMBLY FOR CATHETER PUMP," filed on Mar. 13, 2013, the entire contents of each of which are incorporated herein for all purposes by reference.

As explained above, the impeller assembly 116A can include an expandable cannula or housing and an impeller with one or more blades. As the impeller rotates, blood can be pumped proximally (or distally in some implementations) to function as a cardiac assist device.

In various embodiments, the pump is configured to be primed with fluid. Turning to FIG. 1B, a priming apparatus 1400 can be disposed over the pump assembly 100A including impeller assembly 116A near the distal end portion 170A of the elongate body 174A. The priming apparatus 1400 can be used in connection with a procedure to expel air from the pump assembly 100A and the distal end of the catheter 101, e.g., any air that is trapped within the housing or that remains within the elongate body 174A near the distal end 170A. For example, the priming procedure may be performed before the pump is inserted into the patient's vascular system, so that air bubbles are not allowed to enter and/or injure the patient. The priming apparatus 1400 can include a primer housing 1401 configured to be disposed around both the elongate body 174A and the impeller assembly 116A. A sealing cap 1406 can be applied to the proximal end 1402 of the primer housing 1401 to substantially seal the priming apparatus 1400 for priming, i.e., so that air does not proximally enter the elongate body 174A and also so that priming fluid does not flow out of the proximal end of the housing 1401. The sealing cap 1406 can couple to the primer housing 1401 in any way known to a skilled artisan. In some embodiments, the sealing cap 1406 is threaded onto the primer housing by way of a threaded connector 1405 located at the proximal end 1402 of the primer housing 1401. The sealing cap 1406 can include a sealing recess disposed at the distal end of the sealing cap 1406. The sealing recess can be configured to allow the elongate body 174A to pass through the sealing cap 1406.

The priming operation can proceed by introducing fluid into the sealed priming apparatus 1400 to expel air from the impeller assembly 116A and the elongate body 174A. Fluid can be introduced into the priming apparatus 1400 in a variety of ways. For example, fluid can be introduced distally through the elongate body 174A into the priming apparatus 1400. In other embodiments, an inlet, such as a luer, can optionally be formed on a side of the primer housing 1401 to allow for introduction of fluid into the priming apparatus 1400. A gas permeable membrane can be disposed on a distal end 1404 of the primer housing 1401. The gas permeable membrane can permit air to escape from the primer housing 1401 during priming. In one embodiment, the priming tube and pump may be tilted in a manner to allow trapped air to migrate toward the membrane.

The priming apparatus 1400 also can advantageously be configured to collapse an expandable portion of the catheter pump 100A. The primer housing 1401 can include a funnel 1415 where the inner diameter of the housing decreases from distal to proximal. The funnel may be gently curved such that relative proximal movement of the impeller housing causes the impeller housing to be collapsed by the funnel 1415. During or after the impeller housing has been fully collapsed, the distal end 170A of the elongate body 174A can be moved distally relative to the collapsed housing. After the impeller housing is fully collapsed and retracted into the elongate body 174A of the sheath assembly, the catheter pump 100A can be removed from the priming apparatus 1400 before a percutaneous heart procedure is performed, e.g., before the pump 100A is activated to pump blood. The embodiments disclosed herein may be implemented such that the total time for infusing the system is minimized or reduced. For example, in some implementations, the time to fully infuse the system can be about six minutes or less. In other implementations, the time to infuse can be about three minutes or less. In yet other implementations, the total time to infuse the system can be about 45 seconds or less. It should be appreciated that lower times to infuse can be advantageous for use with cardiovascular patients. Although the described pump is primed with fluid, one will appreciate from the description herein that the priming may be optional. For example, the pump can be prepared such that all air is removed before it is packaged. In another example, air is removed by placing the pump under vacuum.

With continued reference to FIG. 1B, the elongate body 174A extends from the impeller assembly 116A in a proximal direction to a proximal end 195 of the outer sheath to a fluid supply device 1445. The fluid supply device 1445 is configured to allow for fluid to enter the catheter assembly 101 of the catheter pump 100A and/or for waste fluid to leave the catheter assembly 101 of the catheter pump 100A. A catheter body 120A (which also passes through the elongate body 174A) can extend proximally and couple to the motor assembly 1. As discussed in more detail herein, the motor assembly 1 can provide torque to a drive shaft that extends from the motor assembly 1 through the catheter body 120A to couple to an impeller shaft at or proximal to the impeller assembly 116A. The catheter body 120A can pass within the elongate body 174A such that the external elongate body 174A can axially translate relative to the internal catheter body 120A.

Further, as shown in FIG. 1B, a fluid supply line 6 can fluidly couple with the console 122 to supply saline or other fluid to the catheter pump 100A. The saline or other fluid can pass through an internal lumen of the internal catheter body 120A and can provide lubrication to the impeller assembly 116A and/or chemicals to the patient. The supplied fluid (e.g., saline, dextrose, glucose solution, or infusate) can be supplied to the patient by way of the catheter body 120A at any suitable flow rate. For example, in various embodiments, the fluid is supplied to the patient at a flow rate in a range of 15 mL/hr to 50 mL/hr, or more particularly, in a range of 20 mL/hr to 40 mL/hr, or more particularly, in a range of 25 mL/hr to 35 mL/hr. One or more electrical conduits 124 can provide electrical communication between the console 122 and the motor assembly 1. A controller within the console 122 can control the operation of the motor assembly 1 during use.

Fluid (e.g., saline) can be provided from outside the patient (e.g., by way of one or more supply bags 1500) to the pump through a supply lumen in the catheter body. The fluid can return to the motor assembly 1 by way of a lumen (e.g., a central or interior lumen) of the catheter body. For example, as explained herein, the fluid can return to the motor assembly 1 through the same lumen in which the drive shaft is disposed. In addition, a waste line 7 can extend from the motor assembly 1 to a waste reservoir 126. Waste fluid from the catheter pump 100A can pass through the motor assembly 1 and out to the reservoir 126 by way of the waste line 7. In various embodiments, the waste fluid flows to the motor assembly 1 and the reservoir 126 at a flow rate which is lower than that at which the fluid is supplied to the patient. For example, some of the supplied fluid may flow out of the catheter body 120A and into the patient by way of one or more bearings. The waste fluid (e.g., a portion of the fluid which passes proximally back through the motor from the patient) may flow through the motor assembly 1 at any suitable flow rate, e.g., at a flow rate in a range of 5 mL/hr to 20 mL/hr, or more particularly, in a range of 10 mL/hr to 15 mL/hr. Although described in terms of fluid and waste lines, one will appreciate that the pump and motor be configured to operate without fluid flushing. One purpose of the fluid supply is to cool the motor. In the case of a micromotor dimensioned and configured to be inserted percutaneously, there may not be a need for fluid cooling because the motor heat will be dissipated by the body.

Figure 1D:
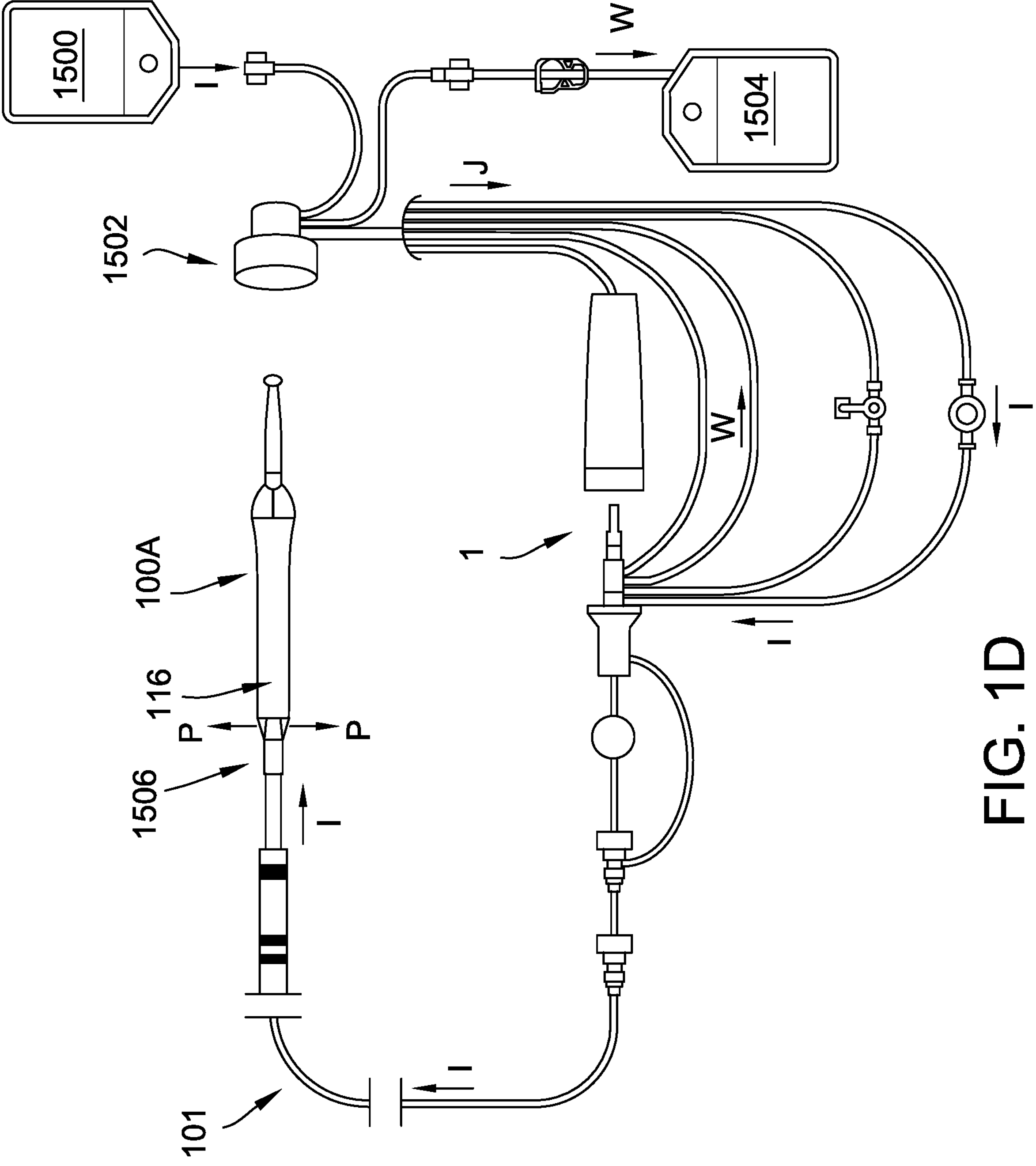
FIG. 1D is a schematic view of another embodiment of a catheter pump system.

Another embodiment is shown with reference to FIG. 1D. The apparatus shown in FIG. 1D is similar to FIG. 1C, except where noted. In this embodiment, a fluid supply 1500, such as a saline supply bag, is in fluid communication with a fluid inflow path I (denoted by arrows). The inflowing saline is pumped through the inflow path I using a pump assembly 1502, which may be referred to as a "puck." In some embodiments, the puck is configured to be placed with the console 122 (FIG. 1B), for example to make electrical and/or fluid connections. In one embodiment, the fluid inflow path I provides fluid to lubricate one or more of the drive cable and bearings of pump assembly 100A. In one embodiment, a portion of the fluid exits the pump assembly 100A at exits P after being used to lubricate and/or cool portions of the pump assembly 100A. In addition, some of the fluid is returned to a waste bag 1504 (which may be the same as or similar to waste reservoir 126 of FIG. 1B) via a fluid waste path W (which may be similar to waste line 7 of FIG. 1B). In one embodiment, approximately 50% of the fluid exits the pump assembly 100A at exits P and approximately 50% of the fluid is returned to waste bag 1504 via waste path W.

Access can be provided to a proximal end of the catheter assembly 101 of the catheter pump 100A prior to or during use. In one configuration, the catheter assembly 101 is delivered over a guidewire 235. The guidewire 235 may be conveniently extended through the entire length of the catheter assembly 101 of the catheter pump 100A and out of a proximal end 1455 of the catheter assembly 101. In various embodiments, the connection between the motor assembly 1 and the catheter assembly 101 is configured to be permanent, such that the catheter pump, the motor housing and the motor are disposable components. However, in other implementations, the coupling between the motor housing and the catheter assembly 101 is disengageable, such that the motor and motor housing can be decoupled from the catheter assembly 101 after use. In such embodiments, the catheter assembly 101 distal of the motor can be disposable, and the motor and motor housing can be re-usable.

In addition, FIG. 1B illustrates the guidewire 235 extending from a proximal guidewire opening 237 in the motor assembly 1. Before inserting the catheter assembly 101 of the catheter pump 100A into a patient, a clinician may insert the guidewire 235 through the patient's vascular system to the heart to prepare a path for the impeller assembly 116A to the heart. In some embodiments, the catheter pump 100A can include a guidewire guide tube 20 (see FIG. 3) passing through a central internal lumen of the catheter pump 100A from the proximal guidewire opening 237. The guidewire guide tube 20 can be pre-installed in the catheter pump 100A to provide the clinician with a preformed pathway along which to insert the guidewire 235.

In one approach, the guidewire 235 is placed into a peripheral blood vessel, and along the path between that blood vessel and the heart and into a heart chamber, e.g., into the left ventricle. Thereafter, a distal end opening of the catheter pump 100A and guidewire guide tube 20 can be advanced over the proximal end of the guidewire 235 to enable delivery of the catheter pump 100A. After the proximal end of the guidewire 235 is urged proximally within the catheter pump 100A and emerges from the guidewire opening 237 and/or guidewire guide tube 20, the catheter pump 100A can be advanced into the patient. In one method, the guidewire guide tube 20 is withdrawn proximally while holding the catheter pump 100A.

Alternatively, the clinician can insert the guidewire 235 through the proximal guidewire opening 237 and urge the guidewire 235 along the guidewire guide tube. The clinician can continue urging the guidewire 235 through the patient's vascular system until the distal end of the guidewire 235 is positioned in the desired position, e.g., in a chamber of the patient's heart, a major blood vessel or other source of blood. As shown in FIG. 1B, a proximal end portion of the guidewire 235 can extend from the proximal guidewire opening 237. Once the distal end of the guidewire 235 is positioned in the heart, the clinician can maneuver the impeller assembly 116A over the guidewire 235 until the impeller assembly 116A reaches the distal end of the guidewire 235 in the heart, blood vessel or other source of blood. The clinician can remove the guidewire 235 and the guidewire guide tube. The guidewire guide tube can also be removed before or after the guidewire 235 is removed in some implementations. After removing at least the guidewire 235, the clinician can activate the motor assembly 1 to rotate the impeller and begin operation of the pump 100A.

In yet another embodiment, catheter pump 100A is configured to be inserted using a modified Seldinger technique. The pump may be configured with a lumen therethrough for receiving a guidewire. Unlike the embodiment described above, however, the guidewire is threaded through the pump without a guidewire guide tube. One will appreciate from the description herein that other configurations may be employed for loading the pump onto a guidewire and/or moving the pump to the target location in the body. Examples of similar techniques are described in U.S. Pat. No. 7,022,100 and U.S. Pub. No. 2005/0113631, the entire contents of which patent and publication are incorporated herein by reference for all purposes.

Figure 2:
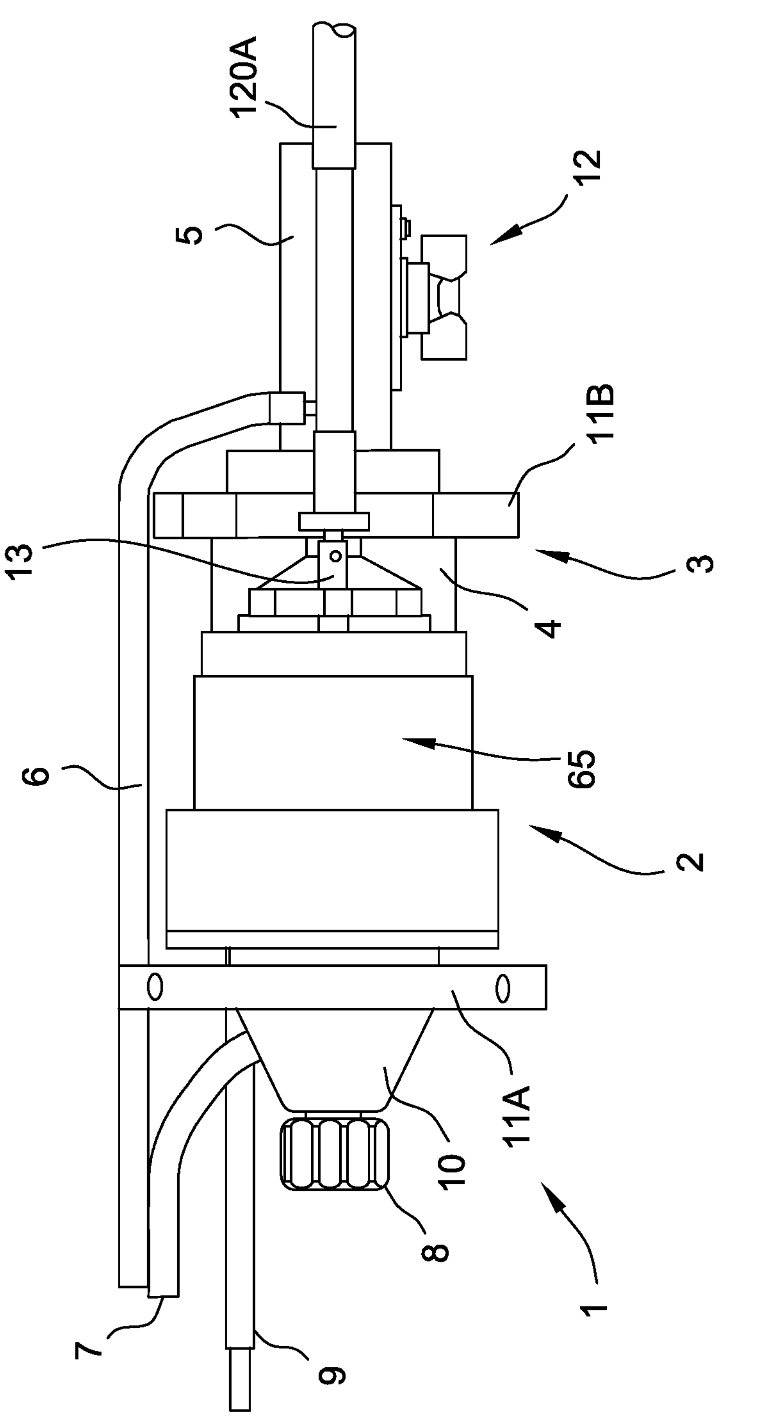
FIG. 2 is a side plan view of a motor assembly of the catheter pump system shown in FIG. 1B, according to various embodiments.
Figure 3:
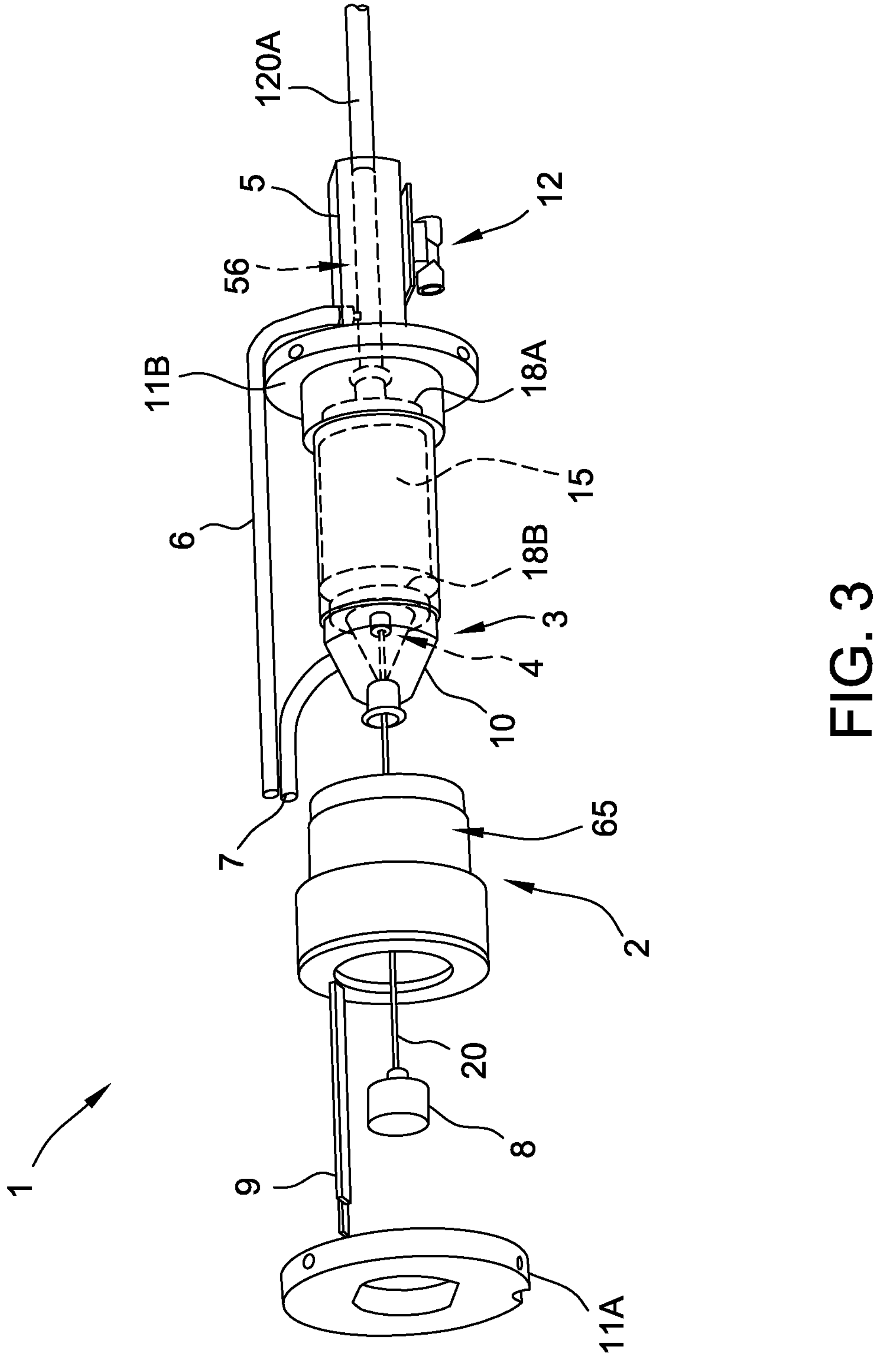
FIG. 3 is a perspective exploded view of the motor assembly shown in FIG. 2.

FIGS. 2 and 3 further illustrate aspects of embodiments of the motor assembly 1 shown in FIG. 1B. The motor assembly 1 can include a stator assembly 2 (FIGS. 2-3) and a rotor 15 disposed radially within the stator assembly 2 (FIG. 3). The motor assembly 1 also includes a flow diverter 3, which can be configured as a manifold for directing fluid through one or more passages in the catheter pump 100A. In some cases, the flow diverter 3 is at least partially disposed radially between the stator assembly 2 and the rotor 15 (FIGS. 2-3). The flow diverter 3 can be fluidly sealed about the rotor 15 and a proximal portion 56 of the catheter body 120A. The seal prevents leakage and also can prevent the fluid from contacting the stator assembly 2. The flow diverter 3 can include a distal chamber 5 within which the proximal portion 56 of the catheter body 120A is disposed and a rotor chamber 4 within which the rotor 15 is disposed. The distal chamber 5 is fluidly connected with the catheter. The rotor chamber 4 is fluidly connected with the waste line 7. The flow diverter 3 can also have a proximal chamber 10 in some embodiments. Where provided, the distal chamber 5, rotor chamber 4, and proximal chamber 10 can be in fluid communication within the flow diverter 3. One or more flanges 11A, 11B can mechanically couple the flow diverter 3 to an external housing (not shown). The flanges 11A, 11B are examples of mount structures that can be provided, which can include in various embodiments dampers to isolate the motor assembly 1 from external shock or vibration. In some embodiments, mount structures can include dampers configured to isolate an outer housing or the environment external to the motor assembly 1 from shock or vibration generated by the motor assembly 1. Further, an optional pressure sensor assembly 12 is configured to measure the pressure at a distal portion of the catheter pump 100A by, for example, measuring the pressure of a column of fluid that extends distally through a lumen of the catheter body 120A. In addition, the guidewire guide tube 20 can extend proximally through the motor assembly 1 and can terminate at a tube end cap 8. As explained above, the guidewire 235 can be inserted within the guide tube 20 for guiding the catheter pump 100A to the heart.

In various embodiments, the rotor 15 and stator assembly 2 are configured as or are components of a frameless-style motor for driving the impeller assembly 116A at the distal end of the pump 100A. For example, the stator assembly 2 can comprise a stator and a plurality of conductive windings producing a controlled magnetic field. The windings can be wrapped about or in a stationary portion 65 of the stator assembly 2. The rotor 15 can comprise a magnetic material, e.g., can include one or more permanent magnets. In some embodiments, the rotor 15 can comprise a multi-pole magnet, e.g., a four-pole or six-pole magnet. Providing changing electrical currents through the windings of the stator assembly 2 can create magnetic fields that interact with the rotor 15 to cause the rotor 15 to rotate. This is commonly referred to as commutation. The console 122 can provide electrical power (e.g., 24V) to the stator assembly 2 to drive the motor assembly 1. One or more leads 9 can electrically communicate with the stator assembly 2, e.g., with one or more Hall sensors used to detect the speed and/or position of the motor. In other embodiments, other sensors (e.g., optical sensors or Back EMF) can be used to measure motor speed. The rotor 15 can be secured to an output shaft 13 (which can comprise a hollow shaft with a central lumen) such that rotation of the rotor 15 causes the output shaft 13 to rotate. In various embodiments, the motor assembly 1 can comprise a direct current (DC) brushless motor. In other embodiments, other types of motors can be used, such as AC motors, gearhead motor, etc.

As shown in FIG. 3, first and second bearings 18A, 18B can be provided about the output shaft 13 to radially and/or longitudinally center the output shaft 13 and thereby the rotor 15 relative to the stator assembly 2. The bearings 18A, 18B can be, for example, journal bearings or ball bearings. In the example, the bearings 18A, 18B facilitate smooth rotation of output shaft 13 and rotor 15. A lubrication fluid can be provided within rotor chamber 4 to lubricate the bearings 18A, 18B.

Figure 4A:
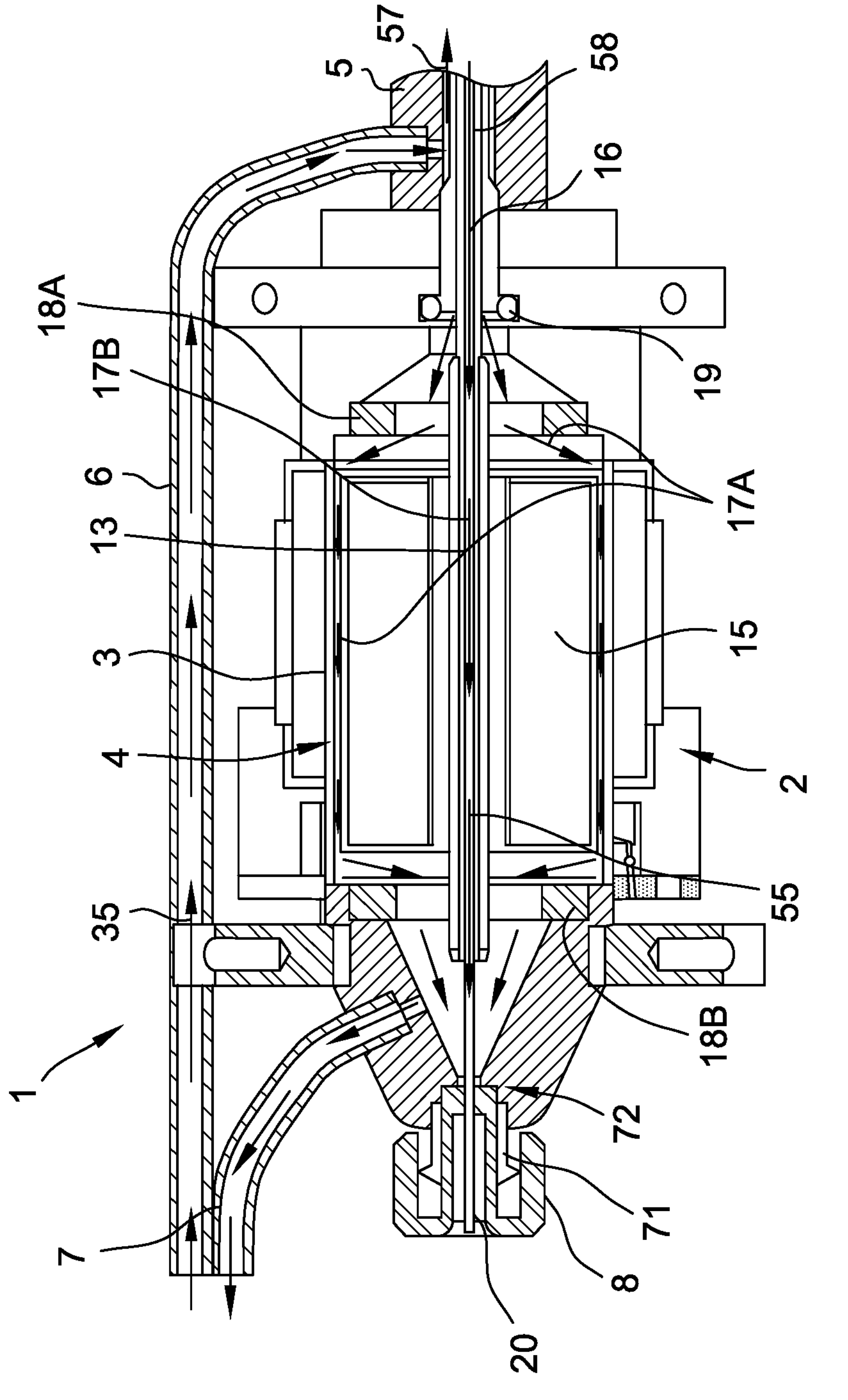
FIG. 4A is a side cross-sectional view of the motor assembly shown in FIGS. 2-3.

FIG. 4A shows that the output shaft 13 (which is secured to the rotor 15) can be mechanically coupled with the proximal end portion of a drive shaft 16. The drive shaft 16 extends distally through an internal lumen of the catheter body 120A. A distal end portion of the drive shaft 16 is mechanically connected with the impeller. Thus, rotation of the rotor 15 causes the output shaft 13 to rotate, which, in turn, causes the drive shaft 16 and the impeller to rotate. FIG. 4A also shows that a lumen 55 can extend through the output shaft 13 and the rotor 15. In certain embodiments, the lumen 55 is coupled with a lumen of the catheter body 120A such that the guidewire guide tube 20 can extend through the lumen 55 within the rotor 15 and into the lumen of the catheter body 120A. In addition, the drive shaft 16 comprises a braided shaft having an internal lumen. The braided drive shaft 16 or cable can be permeable to liquid such that supply fluid or waste fluid can flow from outside the drive shaft 16 to within the internal lumen of the drive shaft 16 (and vice versa).

Figure 7:
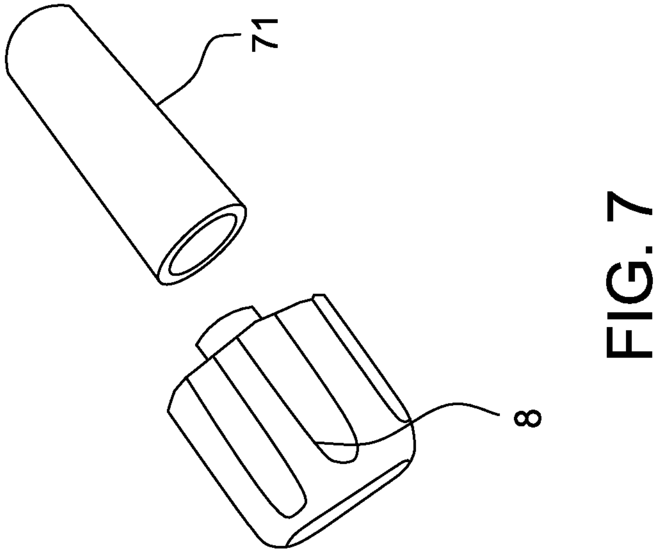
FIG. 7 is an image of a cap and a female receiver, with the guide tube not shown.

FIG. 4A shows the tube end cap 8 welded or otherwise secured to a proximal end portion of the guide tube 20. The cap 8 can be removably engaged (e.g., screwed or otherwise removably locked) over a female receiver 71 that is secured in a proximal end of the proximal chamber 10. For example, the proximal end of the female receiver 71 can be disposed in a counterbore of the cap 8, while the guide tube 20 extends through the central opening of the cap 8. In a locked configuration, one or more tabs of the receiver 71 can be rotated such that the tab(s) slide under a corresponding tab in the counterbore of the cap 8. In an unlocked configuration, the tab(s) of the receiver 71 can be rotated relative to the tabs of the cap 8. FIG. 7 shows one embodiment of the cap 8 and of the female receiver 71 that can be coupled with the guide tube 20 (not shown). In the illustrated embodiment, the cap 8 can be fixed to the guide tube 20; in other embodiments, the receiver 71 can be fixed to the guide tube 20. Engaging the cap 8 to the receiver 71 can advantageously prevent the guide tube 20 from accidentally being removed from or slid within the catheter pump 100A, e.g., if the patient or clinician impacts the cap 8. To remove the guide tube 20 (e.g., after delivery of the impeller assembly 116A to the heart), the clinician can disengage the cap 8 from the receiver 71 and can pull the guide tube 20 from the catheter pump 100A, for example, by pulling proximally on the end cap 8. A resealable septum 72 (e.g., a resealable closure member) can be provided at the proximal end of the flow diverter 3, e.g., near the distal end of the cap 8 when the cap 8 is in place. When the guidewire guide tube 20 is removed from the pump 100A, the septum 72 will naturally reseal the pathway proximally from the motor assembly 1 such that fluid does not exit the assembly 1. An advantage of the assembly described herein is that the cap 8 is locked and will not be dislodged without rotating and unlocking cap 8 from receiver 71. Otherwise, the cap 8 can slide axially if it is inadvertently bumped by the patient or clinician. This potentially results in the guide tube 20 being pulled out from the distal-most end of the impeller assembly 116A, and because the guide tube cannot be re-inserted, the clinician either has to use the catheter pump 100A without a guide or get a new pump.

With continued reference to FIG. 4A, it can be important to ensure that the motor assembly 1 is adequately cooled. In various embodiments, it can be important to provide a heat removal system to limit buildup of heat in the motor assembly 1 during operation. For example, it can be important to maintain external surfaces of the motor assembly 1 at a temperature less than about 40° C. if the motor assembly 1 is positioned near the patient. For example, an external surface of an external housing of the motor assembly 1 may be kept at or below this temperature. In some respects, regulatory guidelines can require that no part in contact with skin exceed 40° C. To that end, various strategies for heat management are employed by the inventions described herein. It should be appreciated that, as used herein, cooling refers to transferring away or dissipating heat, and in certain respects, cooling is used interchangeably with removing heat. In some embodiments, however, the fluids passing through or around the motor assembly 1 may not be utilized for cooling purposes.

Various components of the motor assembly 1 generate heat. For example, moving parts within the motor assembly 1 (e.g., the rotating output shaft 13 and/or drive shaft 16) can generate heat by virtue of losses through friction, vibrations, and the like, which may increase the overall temperature of the motor assembly 1. Further, heat can be generated by the electrical current flowing through the stator assembly 2 and/or by induction heating caused by conductive components inside a rotating magnetic field. Furthermore, friction between the bearings 18A, 18B and the output shaft 13 and/or friction between the drive shaft 16 and the inner wall of catheter body 120A may also generate undesirable heat in the motor assembly. Inadequate cooling can result in temperature increases of the motor assembly 1, which can present patient discomfort, health risks, or performance losses. This can lead to undesirable usage limitations and engineering complexity, for example, by requiring mitigation for differential heat expansion of adjacent components of different materials. Accordingly, various embodiments disclosed herein can advantageously transfer away generated heat and cool the motor assembly 1 such that the operating temperature of the assembly 1 is sufficiently low to avoid such complexities of use or operation and/or other components of the system. For example, various heat transfer components can be used to move heat away from thermal generation sources and away from the patient. Various aspects of the illustrated device herein are designed to reduce the risk of hot spots, reduce the risk of heat spikes, and/or improve heat dissipation to the environment and away from the patient.

In some embodiments, the catheter pump makes use of the fluid supply system already embedded in the pump to cool the motor assembly 1 and housing. In some embodiments, heat absorbing capacity of fluid flowing through the flow diverter 3 is used to cool the motor assembly 1. As shown in FIG. 4A, the supply line 6 can supply fluid 35 from a source (e.g., a fluid bag) to an outer lumen 57 of the catheter body 120A. The supplied fluid 35 can travel distally toward the impeller assembly 116A to lubricate rotating components in the catheter assembly 101 and/or supply fluid to the patient. A seal 19 (e.g., an O-ring) can be provided between the rotor chamber 4 and the distal chamber 5 to prevent backflow of the fluid 35 into the rotor chamber 4. In this context, backflow is flow of fluid 35 proximally into the distal chamber 5 rather than distally within the lumen 57. Such flow is to be prevented to ensure that the fluid 35 is initially exposed to moving parts in a distal portion of the catheter assembly 101 to lubricate and cool such distal components.

Fluid from the catheter pump 100A can flow proximally through an inner lumen 58 of the catheter body 120A. For example, after initially cooling distal components some or all of the supplied fluid 35 can flow within the drive shaft 16 and/or around the periphery of the drive shaft 16. After initially cooling distal components some or all of the supplied fluid 35 can flow in a space disposed radially between the drive shaft 16 and the catheter body 120A. The proximally-flowing fluid can flow along a flow pathway which removes heat from the motor assembly 1. As shown in FIG. 4A, the proximally-flowing fluid (or other cooling fluid) can flow into the rotor chamber 4 of the flow diverter 3. A first portion 17A of the waste fluid can pass proximally through the motor assembly 1 about a periphery of the rotor 15, e.g., in a gap between the rotor 15 and a wall of the flow diverter 3. In some embodiments, a second portion 17B of the waste fluid can pass proximally through the motor assembly 1 through the lumen 55 of the output shaft 13. The fluid portions 17A, 17B can pass from the rotor chamber 4 into the proximal chamber 10 of the flow diverter 3, where the fluid 17A, 17B can flow out to a reservoir (not shown) by way of line 7.

The embodiment of FIG. 4A can advantageously convey heat from the heat generating components (e.g., rotor 15 and stator assembly 2) into the fluid 35 or other cooling fluid and to the reservoir 126 by way of the waste line 7. For example, the first portion 17A of the fluid that passes about the periphery of the rotor 15 can direct heat radially outward from the rotor 15 and other components of the flow diverter 3. The first portion 17A of the fluid that passes about the periphery of the rotor 15 can direct heat inward from the stator assembly 2 and other components outside the flow diverter 3. The second portion 17B of the waste fluid can draw heat radially inward, e.g., radially inward from the rotor 15 and other components of the flow diverter 3. As the heat from the motor assembly 1 is conveyed away by way of the fluid to the reservoir 126, the temperature of the motor housing can be reduced or maintained at a suitable operational temperature for the medical staff, the patient and/or for the catheter pump system. A gap between the stator assembly and the external motor housing (e.g., the outer shell or housing surrounding the motor assembly) comprises air (which has the added benefit of being readily available and a good, natural insulator) or inert gas. Thus, the heat from the stator assembly 2 is naturally transferred to the waste line rather than dissipating out the sides of the housing of the motor assembly 1.

Figure 4B:
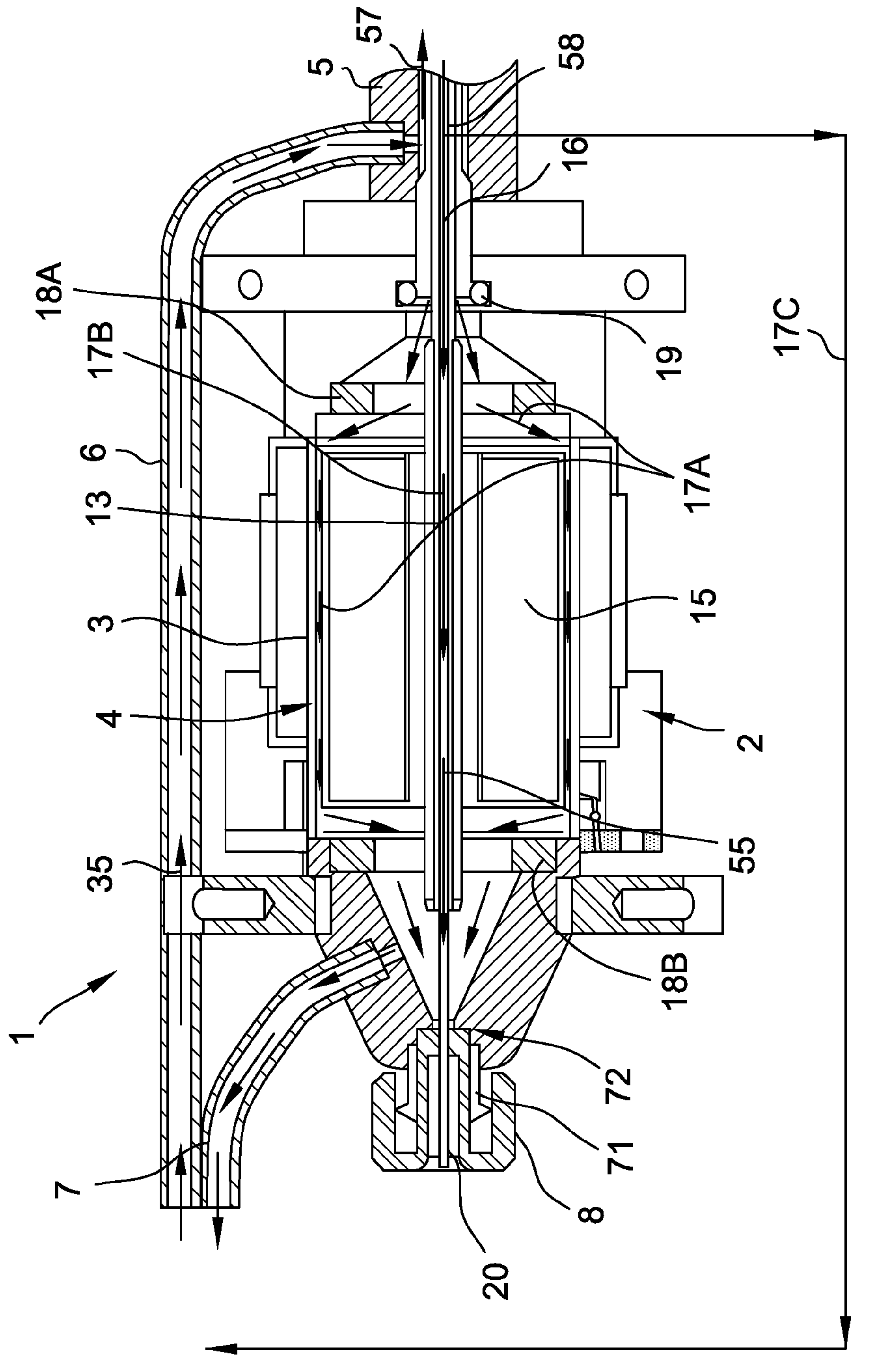
FIG. 4B is a side cross-sectional view of a motor assembly, according to another embodiment.

FIG. 4B is a side cross-sectional view of a motor assembly 1, according to another embodiment. Unless otherwise noted, components numbered similar to those in FIG. 4A represent the same or similar components and functionalities. For example, as with the embodiment of FIG. 4A, in the embodiment of FIG. 4A, a first portion 17A of the fluid can pass proximally through the motor assembly 1 about a periphery of the rotor 15, e.g., in a gap between the rotor 15 and a wall of the flow diverter 3. In some embodiments, a second portion 17B of the fluid can pass proximally through the motor assembly 1 through the lumen 55 of the output shaft 13. The fluid portions 17A, 17B can pass from the rotor chamber 4 into the proximal chamber 10 of the flow diverter 3, where the fluid 17A, 17B can flow out to a reservoir (not shown) by way of line 7. Thus, the fluid portions 17A, 17B can flow along a first fluid pathway or channel within the flow diverter 3 which is disposed inside the stator assembly 2.

Unlike the embodiment of FIG. 4A, however, in the embodiment of FIG. 4B, a third portion 17C of the fluid can be shunted around the rotor 15 and stator assembly 2 along a second fluid pathway or channel. For example, as shown in FIG. 4B, the third portion 17C of the proximally-flowing fluid can be withdrawn from the inner lumen 58 of the catheter body 120A by way of a suitable conduit and fluid connector. The third fluid portion 17C can bypass the motor assembly 1. The fluid can then be conveyed to the waste reservoir by a suitable waste line, which may be the same as or different from the waste line 7. The third portion 17C of the proximally-flowing fluid can be more than, less than, or about the same in volume as the combined volume of the first and second fluid portions 17A, 17B. In other embodiments, rather than being conveyed directly to a waste line, the third portion 17C can be transported by a conduit to a heat exchanger to further cool the motor assembly 1. For example, the third fluid portion 17C can be conveyed to coiled tubing or a tubular sleeve disposed about the stator assembly 2, as shown in various embodiments of the following concurrently filed application: application Ser. No. 15/003,682, entitled "MOTOR ASSEMBLY WITH HEAT EXCHANGER FOR CATHETER PUMP," which is expressly incorporated by reference herein in its entirety and for all purposes.

The embodiment of FIG. 4B may be desirable in arrangements in which the first and second fluid portions 17A, 17B become too hot and/or otherwise ineffective at cooling the motor assembly 1. For example, in some arrangements, the motor assembly 1 may heat the first and second fluid portions 17A, 17B passing inside the flow diverter 3 to such a degree that the temperatures of the fluid portions 17A, 17B and/or the motor assembly 1 rise to unacceptable levels. In such a situation, it may be desirable to shunt some, most, or all of the proximally-flowing fluid around the motor assembly 1 along the second fluid pathway. For example, in some embodiments, the first and second fluid portions 17A, 17B may pass through the flow diverter 3 along the first fluid pathway at a flow rate less than that provided in the embodiment of FIG. 4A. In the embodiment of FIG. 4A, the fluid may flow back proximally through the flow diverter at rate such that the combined flow rate of the first and second portions 17A, 17B is in a range of 5 mL/hr to 20 mL/hr, or more particularly, in a range of 10 mL/hr to 15 mL/hr.

In the embodiment of FIG. 4B, however, some, most, or all of the proximally-flowing fluid is diverted around the flow diverter 3 and other components of the motor along the second fluid pathway as the third fluid portion 17C. The amount of the fluid portion 17C diverted around the motor assembly 1 can be any suitable amount so as to maintain an adequate external temperature of the motor assembly 1. For example, in one embodiment, the third fluid portion 17C represents a relatively small volume of fluid diverted from the inner lumen 58. In one embodiment, the third fluid portion 17C flows around the motor assembly 1 at a flow rate in a range of 1 mL/hr to 30 mL/hr. In one embodiment, the third fluid portion 17C flows around the motor assembly 1 at a flow rate in a range of 1 mL/hr to 5 mL/hr, or in a range of 1 mL/hr to 3 mL/hr. In one embodiment, the third fluid portion 17C flows around the motor assembly 1 at a flow rate in a range of 10 mL/hr to 50 mL/hr. In another embodiment, the third fluid portion 17C represents a majority of the fluid diverted from the inner lumen 58. For example, in such an embodiment, the third fluid portion 17C may have a flow rate in a range of 5.5 mL/hr to 12 mL/hr, in a range of 5.5 mL/hr to 10 mL/hr, in a range of 5.5 mL/hr to 8 mL/hr, in a range of 5.5 mL/hr to 7 mL/hr, in a range of 10 mL/hr to 14 mL/hr, or in a range of 8 mL/hr to 12 mL/hr. Advantageously, diverting some of the proximally-flowing fluid around the motor assembly 1 can improve the transfer of heat away from the motor assembly 1, for example, in situations in which the first and second fluid portions 17A, 17B become too hot.

Moreover, in some embodiments, the console 122 can be configured to change the amount of the third fluid portion 17C flowing along the second fluid pathway before and/or during a treatment procedure to adjust the volume of fluid that is diverted from the inner lumen 58 around the motor assembly 1. For example, the console 122 can send instructions to a pump (such as a peristaltic pump) to adjust the flow rate of fluid shunted or bypassed around the motor assembly 1. In various respects, the terms "shunted" and "bypassed" are used interchangeably herein. In some embodiments, a common pump is applied to all three fluid portions 17A-17C. In other embodiments, one pump is applied to draw the first and second fluid portions 17A, 17B, and a separate pump is applied to draw the third fluid portion 17C.

In still other embodiments, all or substantially all the fluid flowing proximally through the inner lumen 58 is shunted around the motor assembly 1 along the second fluid pathway. The shunted third fluid portion 17C can be diverted to a waste reservoir and/or to a heat exchanger disposed about the stator assembly 2, as explained above. In such embodiments, all (100%) or substantially all (i.e., between 90% and 100%) of the proximally-flowing fluid does not flow within the motor assembly 1 (e.g., within the flow diverter 3), but is instead diverted around the motor assembly 1. Thus, in some embodiments, there may be no proximally-flowing fluid portions 17A, 17B within the flow diverter 3. In such arrangements, the motor assembly 1 may be adequately cooled without the fluid portions 17A, 17B flowing proximally through the flow diverter 3. The fluid flowing proximally through the inner lumen 58 may also provide sufficient pressure so as to prevent air or other gases from passing distally through the catheter body 120A to the patient.

Advantageously, the embodiments disclosed in FIGS. 1A-4B can adequately remove heat from the motor assembly 1 without requiring the use of external cooling fins exposed to the outside environs. That is, the thermal performance of the heat removal systems disclosed in FIGS. 2-4B can adequately reduce the temperature of the outer surface of the motor housing without using cooling fins exposed outside of the motor housing (e.g., outside of an exterior surface of the motor assembly 1) to the ambient environment. Rather, the heat removal systems may be disposed entirely within the motor housing, e.g., within the housing which encloses the rotor and stator. For example, in some embodiments, the systems disclosed in FIGS. 1A-4B can ensure that the temperature of the exterior surface of the motor assembly 1 is not more than about 40° C. In some embodiments, the systems disclosed in FIGS. 1A-4B can ensure that the temperature of the exterior surface of the motor assembly 1 is in a range of 15° C. to 42° C., or more particularly in a range of 20° C. to 42° C., in a range of 20° C. to 40° C., in a range of 20° C. to 35° C., or in a range of 20° C. to 30° C., without requiring the use of external cooling fins exposed outside the motor housing.

Still other thermal management techniques may be suitable in combination with the embodiments disclosed herein. For example, U.S. Patent Publication Nos. 2014/0031606 and 2011/0295345, which are incorporated by reference herein in their entirety and for all purposes, describe structures and materials which may be incorporated in place of or in addition to the devices described above to dissipate heat effectively, as will be understood by one of skill from the description herein. For example, in embodiments in which the motor is miniaturized so as to be disposed within the patient's body, all or substantially all the fluid may bypass or shunt around the motor. In such embodiments, the miniaturized motor may be sufficiently cooled by the flow of blood passing around the motor and/or motor housing.

Figure 5:
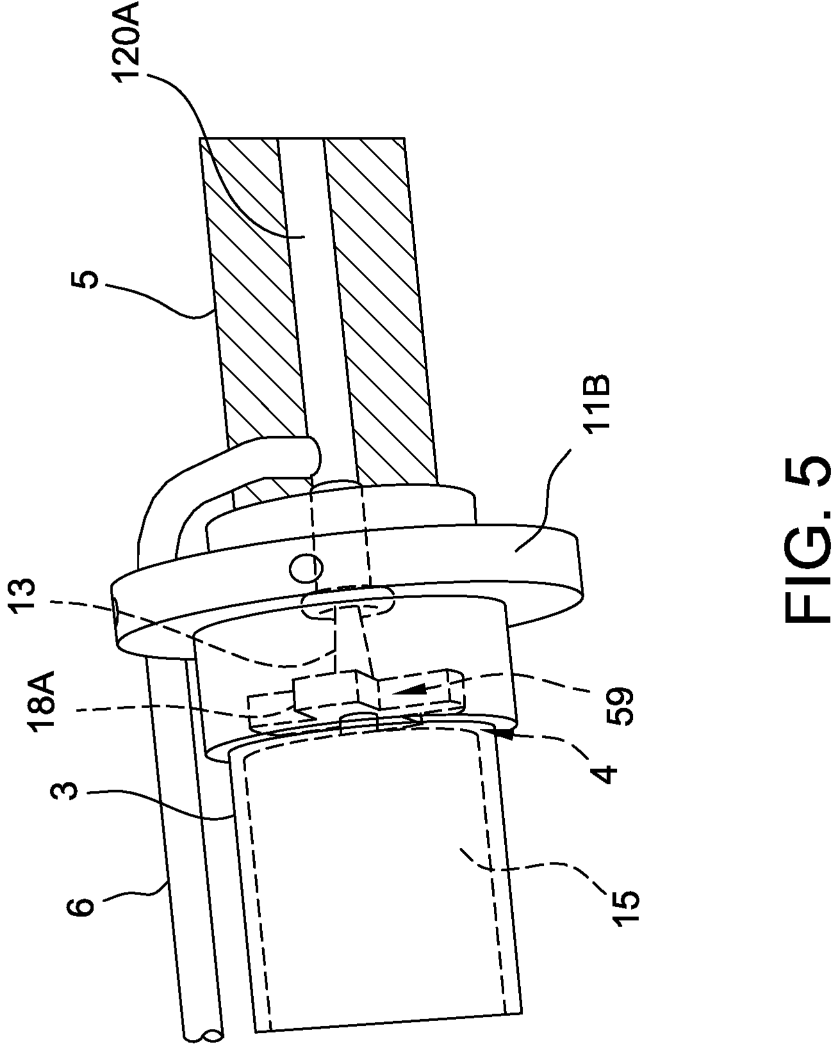
FIG. 5 is a schematic perspective view of an interface between a distal chamber and a rotor chamber of a flow diverter of the motor assembly, with a stator assembly thereof hidden for ease of illustration.

FIG. 5 is a schematic perspective view of an interface between the distal chamber 5 and the rotor chamber 4 of the flow diverter 3, with the stator assembly 2 hidden for ease of illustration. FIG. 5 shows the output shaft 13 coupled with a proximal portion of the drive shaft 16 through an aperture in the flange 11B. The journal bearings 18A (FIGS. 3 and 5) and 18B (FIG. 3) can be provided on opposite axial sides of the rotor 15 to help maintain the rotor 15 in radial alignment with the rotor chamber 4 and/or in axial alignment with the stator assembly 2. Improving radial alignment of the rotor 15 and output shaft 13 relative to the rotor chamber 4 can reduce or eliminate eccentricity during rotation, which can reduce vibrations. Improving axial alignment relative to the stator assembly 2 can advantageously improve the efficiency of the motor assembly 1 by ensuring that the windings of the stator assembly 2 are adequately aligned with the rotor 15. In various embodiments, the bearings 18A, 18B can be rotationally decoupled with the output shaft 13 such that the output shaft 13 can rotate relative to the bearings 18A, 18B. In some embodiments, the journal bearings 18A, 18B can be fixed inside the rotor chamber 4. Moreover, one or more passages 59 can be provided through or across the bearings 18A, 18B so that cooling fluid can pass axially through the bearings 18A, 18B. For example, as shown in FIG. 5, the passages 59 are defined at least in part by a cross-shaped structure of the bearings 18A, 18B, but other variations for the passages 59 may be suitable. For example, the bearings 18A, 18B can form radially-extending arms with one or more gaps disposed between the arms. Such gaps can be enclosed peripherally by a housing enclosing the stator assembly 2. In other embodiments, one or more openings can be provided through the bearings 18A, 18B to define the passages.

Figures 6A, 6B:
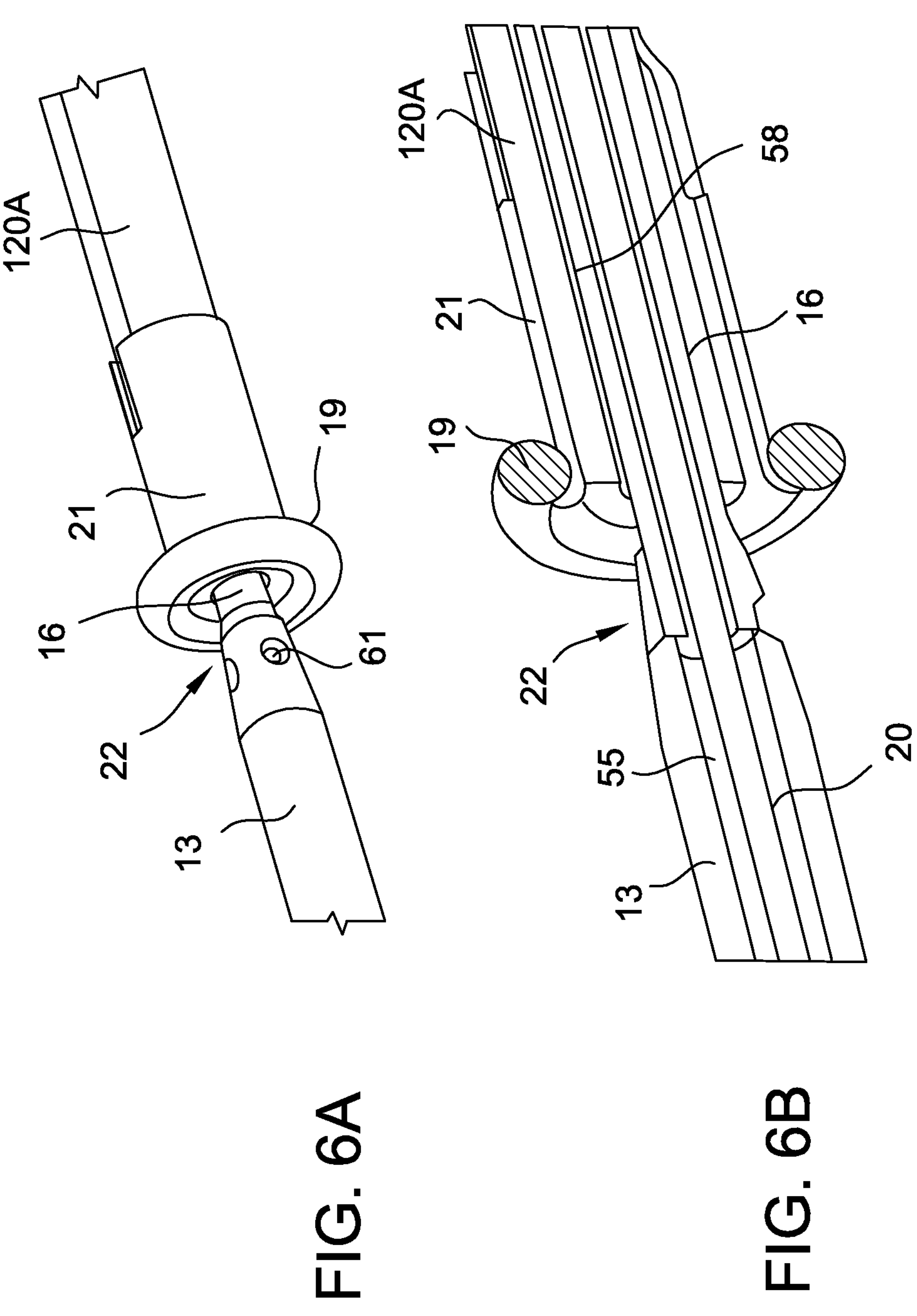
FIG. 6A is a schematic perspective view of an interface between an output shaft of the motor assembly and a drive shaft of the catheter pump system.
FIG. 6B is a cross-sectional perspective view, taken through the longitudinal axis of the catheter, showing the interface shown in FIG. 6A.

FIGS. 6A and 6B show one embodiment of an interface 22 between the output shaft 13 and the drive shaft 16. The interface 22 can comprise a connection between a distal portion of the output shaft 13 and a proximal portion of the drive shaft 16. The distal portion of the output shaft 13 can comprise a radially-inward taper and one or more holes 61 formed through the output shaft 13. The proximal portion of the drive shaft 16 can be inserted within the lumen 55 of the output shaft 13 such that the lumen 55 and the inner lumen 58 of the catheter body 120A form a continuous passage. This passage can be used to advance the guidewire guide tube 20, sensors, and other instruments, or to provide fluid communication for cooling fluid or medications. Cooling fluid can flow proximally from the inner lumen 58 of the catheter body 120A and the first portion 17A of the fluid can pass outwardly about the periphery of the rotor 15. In some embodiments, the second portion 17B of the fluid can pass through the lumen 55 of the output shaft 13. A sleeve 21 can be disposed about the proximal portion of the catheter body 120A, and the seal 19 can be provided about the sleeve 21 to seal the distal chamber 5 from the rotor chamber 4.

In the illustrated embodiments, the output shaft 13 is permanently coupled with, e.g., laser welded to the drive shaft 16. For example, a welding machine can access the interface 22 by way of the holes 61 formed in the output shaft 13 to weld the output shaft 13 to the drive shaft 16. In other embodiments, the output shaft 13 can be secured to the drive shaft 16 in other ways, e.g., by friction or interference fit, by adhesives, by mechanical fasteners, etc.

In some embodiments, the motor assembly 1 shown in FIGS. 1B-1C can be sealed from the fluids (e.g., saline and/or bodily fluids) that pass proximally through the catheter assembly. As explained herein, in some embodiments, the proximally-flowing fluid may flow from the catheter body 120A through a chamber near the motor assembly 1. For example, in the embodiments described above, the proximally-flowing fluid may flow through a chamber in which a portion of the motor assembly (e.g., the rotor) is disposed, such as the flow diverter 3. For example, in some embodiments, the catheter pump system can include a shaft assembly 302 and an impeller coupled with a distal portion of the shaft assembly 302. The catheter pump system can include a motor assembly 1 which imparts rotation on the impeller through the shaft assembly 302. The motor assembly 1 can comprise a motor 300 (e.g., an electric motor such as a direct drive electric motor) which rotates the shaft assembly 302. In some embodiments disclosed herein, a direct drive motor can comprise a motor that lacks a gear reduction and/or a clutch. A fluid pathway can convey fluid (e.g., waste fluid) proximally during operation of the catheter pump system. In some arrangements, a seal 303 can be disposed between the motor assembly 1 and the impeller to impede or prevent proximally-flowing fluids from entering the motor assembly 1 at least about an outer periphery 308 of the shaft assembly 302. In various embodiments, the seal 303 can comprise an opening 309 through which a portion of the shaft assembly 302 extends. For example, in some embodiments, a lumen can comprise a motor lumen extending through at least the motor 300. The lumen can pass through the catheter pump system from a distal end of the catheter pump to a proximal end of the catheter pump system.

Turning to FIGS. 8A-8E, an example of a motor assembly 1 is disclosed, according to some embodiments. The motor assembly 1 of FIGS. 8A-8E may be used in combination with any suitable features disclosed above in connection with FIGS. 1A-7. Unless otherwise noted, like reference numerals refer to components that are the same as or generally similar to the components shown in FIGS. 1A-7.

Figure 8A:
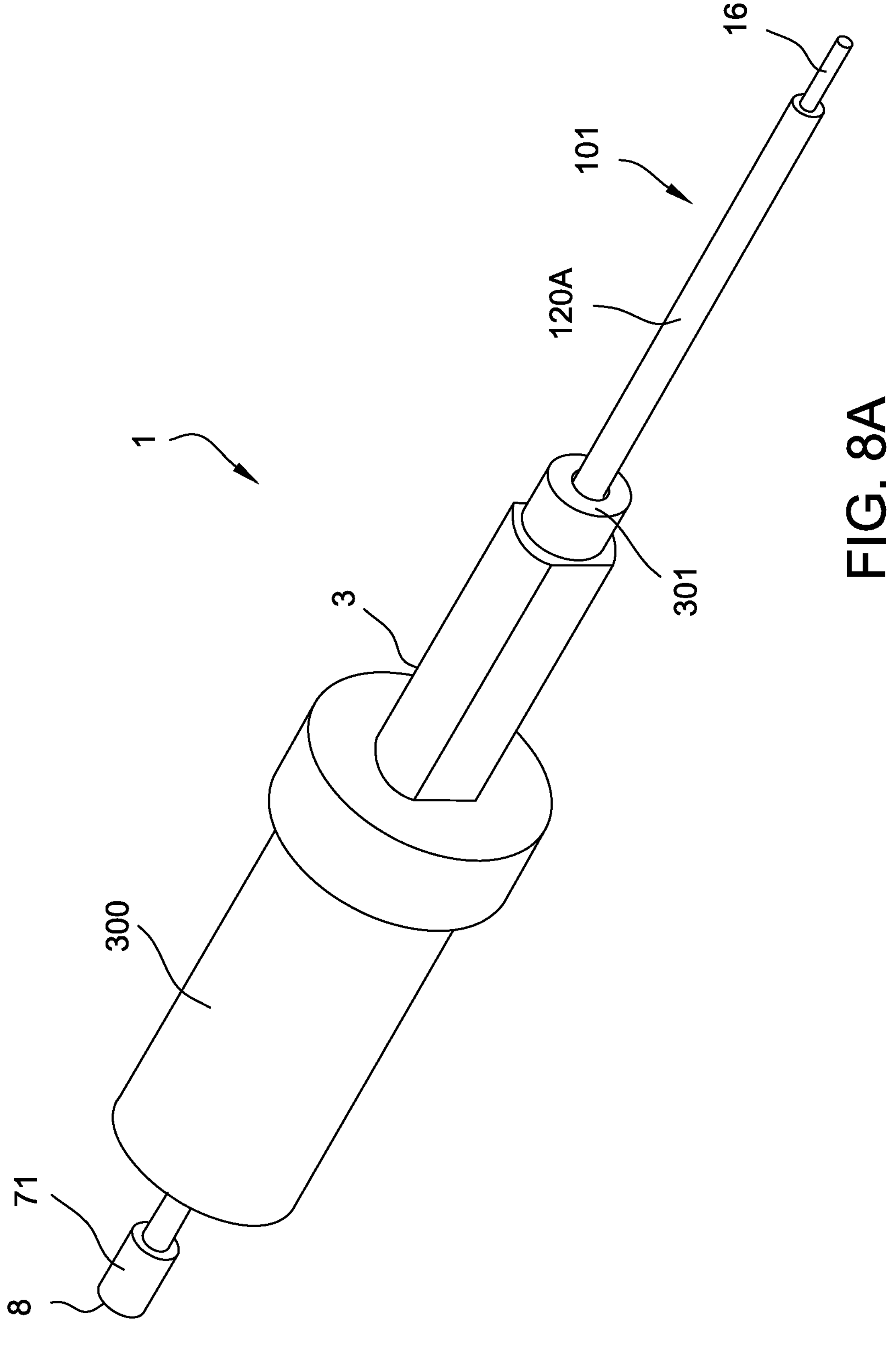
FIG. 8A is a schematic perspective view of a motor assembly, according to another embodiment.

As shown in FIG. 8A, the motor assembly 1 can comprise a catheter assembly 101 comprising a catheter body 120A through which a drive shaft 16 extends. As explained above, the drive shaft 16 can be disposed within an inner lumen 358 (see FIG. 8D) of the catheter body 120A. The drive shaft 16 can comprise a braided wire in various arrangements. In some embodiments, the drive shaft 16 can be hollow, and fluids can flow therethrough. In some embodiments, the drive shaft is formed of braided wire which can be saturated with fluid. The catheter body 120A can be coupled with a chamber near or coupled with the motor assembly 1, such as the flow diverter 3, by way of a retaining cap 301, which can secure the catheter body 120A to the chamber (e.g., flow diverter 3). The motor assembly 1 can comprise a motor 300. The motor 300 can comprise a direct drive electrical motor. The motor can be a direct current (DC) motor. As with the embodiments explained above, an end cap 8 and receiver 71 can be provided at the proximal end of the motor assembly 1 to provide access to an internal lumen within the assembly 1. In various embodiments, the end cap comprises a resealable material, e.g., to provide resealable access for a guidewire guide tube and/or guidewire. It should be appreciated that although the flow diverter 3 is illustrated in FIG. 8A, however, any suitable type of chamber may be disposed distal the motor assembly 1 to direct fluids into and/or out of the catheter assembly.

Figure 8B:
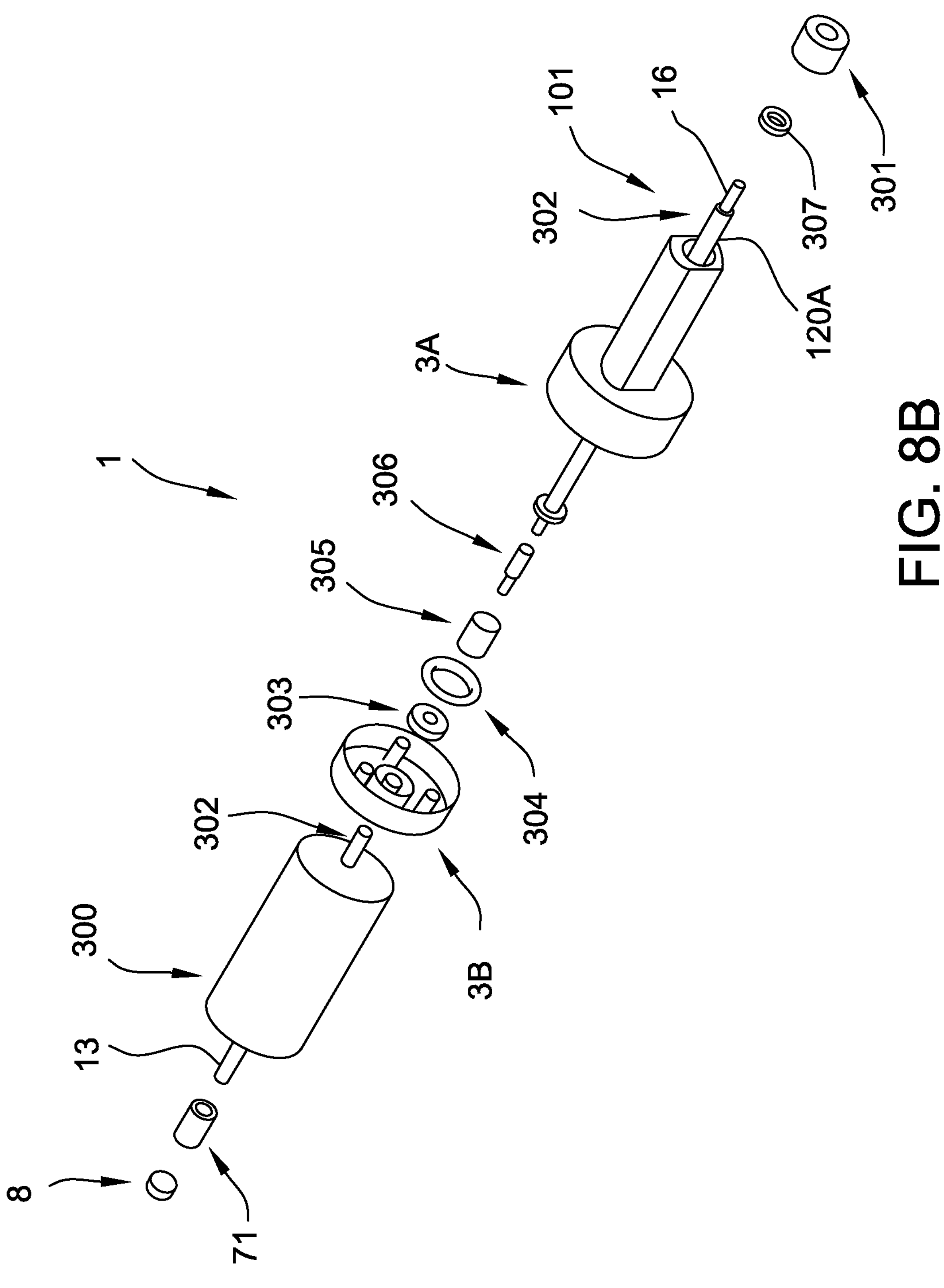
FIG. 8B is a schematic perspective exploded view of the motor assembly of FIG. 8A.
Figures 8C, 8D:
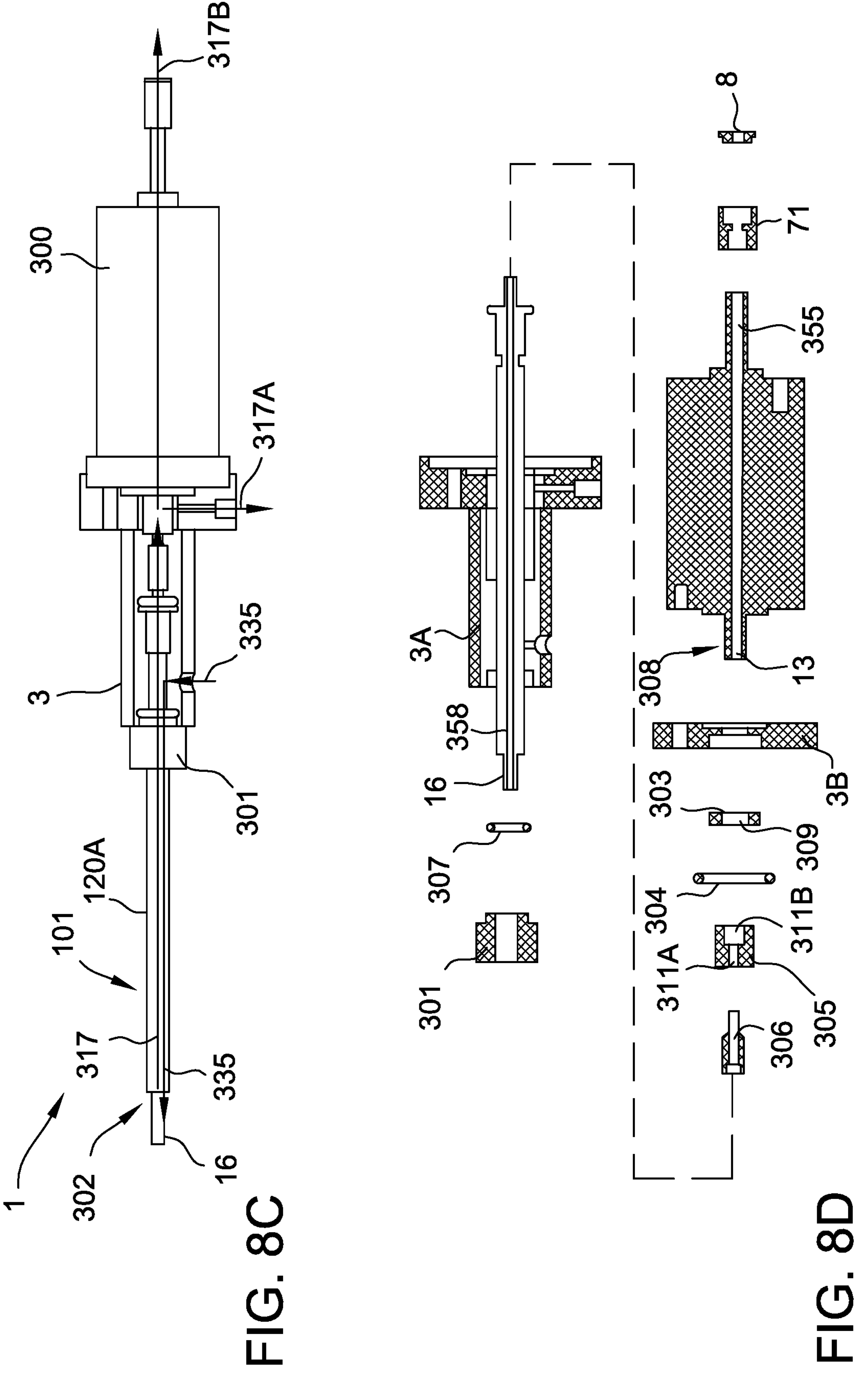
FIG. 8C is a schematic side view of the motor assembly of FIGS. 8A-8B.
FIG. 8D is a schematic side sectional, exploded view of the motor assembly shown in FIG. 8C.

As shown in FIG. 8B, the flow diverter 3 can comprise a distal flow diverter portion 3A and a proximal flow diverter portion 3B. The retaining cap 301 can couple with the distal flow diverter portion 3A with a washer 307 disposed therebetween. For example, the retaining cap 301 and washer 307 can be disposed over the catheter body 120A. As shown in FIGS. 8B-8D, the flow diverter 3 can comprise a chamber in which various components are disposed. For example, as shown in FIG. 8D, a motor coupling 305, a motor adapter 306, a gasket 304, and a seal 303 can be disposed in the chamber of the flow diverter 3.

The motor coupling 305 can connect to a distal end portion of the motor output shaft 13, and can connect to a proximal portion of the motor adapter 306. In some arrangements, the motor coupling 305 can comprise a first opening 311A sized and shaped to receive the proximal portion of the motor adapter 306 therein, and a second opening 311B sized and shaped to receive the distal end portion of the motor output shaft 13. In various embodiments, at least one of the openings 311A, 311B can comprise a polygonal opening, e.g., a rectangular or square opening with at least one flat surface or edge. In the illustrated embodiment, the first opening 311A can comprise a polygonal opening, and the second opening 311B can comprise a rounded opening. In other embodiments, the first opening 311A can comprise a rounded opening, and the second opening 311B can comprise a polygonal opening. In FIG. 8D, the first opening 311A can be fitted about the proximal end portion of the motor adapter 306, and the second opening 311B can be fitted about the distal end portion of the motor output shaft 13. The motor adapter 306 can be mechanically connected to the proximal end portion of the drive shaft 16. The motor 300 can cause the output shaft 13 to rotate, which can in turn cause the motor coupling 305, motor adapter 306, and drive shaft 16 to rotate to impart rotation on the impeller.

As explained above, fluids (such as saline) can flow proximally through the catheter pump system during operation of the impeller. For example, as shown in FIG. 8C, a supply fluid pathway 335 can direct fluid (e.g., saline, infusate, etc.) distally through a lumen disposed within, but in some embodiments located off-center relative to a central longitudinal axis of, the catheter body 120A to provide a lubricant, e.g., saline, to the impeller. A return fluid pathway 317 can be provided along the inner lumen 358 of the catheter body 120A such that proximally flowing fluid flows towards the motor assembly 1 from a distal portion of the device adjacent to the impeller. The return fluid pathway 317 can flow within and/or around the drive shaft 16, which can be disposed inside the inner lumen 358.

In various embodiments, it can be advantageous to prevent or impede fluids from entering the motor 300 and damaging or destroying sensitive components within the motor 300. Accordingly, in the illustrated embodiment, the seal 303 and the gasket 304 can be disposed in the chamber of the flow diverter 3 to prevent or impede fluids from damaging sensitive components of the motor. In some embodiments, some or all of the fluid conveyed along the returning fluid pathway 317 exits the flow diverter 3 by way of a first return pathway 317A. For example, the first return pathway 317A can be in fluid communication with a waste line to convey fluid flowing therein to and along the waste line (such as waste line 7 described above) to a reservoir. The first return pathway 317A may comprise a conduit that directs a portion of the fluid to bypass the motor assembly 1.

In some embodiments, some of the returning fluid (a second fluid pathway 317B) can pass within the lumen 355 of the motor output shaft 13. For example, in such embodiments, the returning fluid 317 can flow through the inner lumen 358 of the catheter body 120A, which can fluidly communicate with the lumen 355 of the motor output shaft 13. Fluid conveyed in the returning fluid pathway 317 can flow proximally within and/or around the drive shaft 16 (which can be disposed inside the inner lumen 358 of the catheter body 120A), through the motor adapter 306, the motor coupler 305, the seal 303, and the proximal flow diverter portion 3B, and into the lumen 355 of the motor output shaft 13. In other embodiments, no or little fluid may flow through the lumen 355 of the output shaft 13.

As shown in FIGS. 8C-8D, the shaft assembly 302 (e.g., including the motor output shaft 13) can extend through at least a portion of the motor 300, through the proximal flow diverter portion 3B, through an opening 309 of the seal 303, and into the motor coupling 305. The shaft assembly 302 (e.g., including the drive shaft 16) can further extend from the motor adapter 306 distally to the impeller assembly. Thus, in the illustrated embodiment, the shaft assembly 302 and a lumen thereof can extend through the seal 303.

As explained herein, a guidewire guide tube (not shown in FIGS. 8A-8E) may be disposed in a lumen which comprises the lumen 355 of the output shaft 13 and the inner lumen 358 of the catheter body 120A. The guidewire guide tube may extend through a lumen which extends between the distal end of the catheter pump system and the proximal end of the catheter pump system (i.e., proximally out the end cap 8). The clinician may insert a guidewire through the guidewire guide tube and may advance the impeller assembly over the guidewire guide tube to a treatment location, as explained above.

Figure 8E:
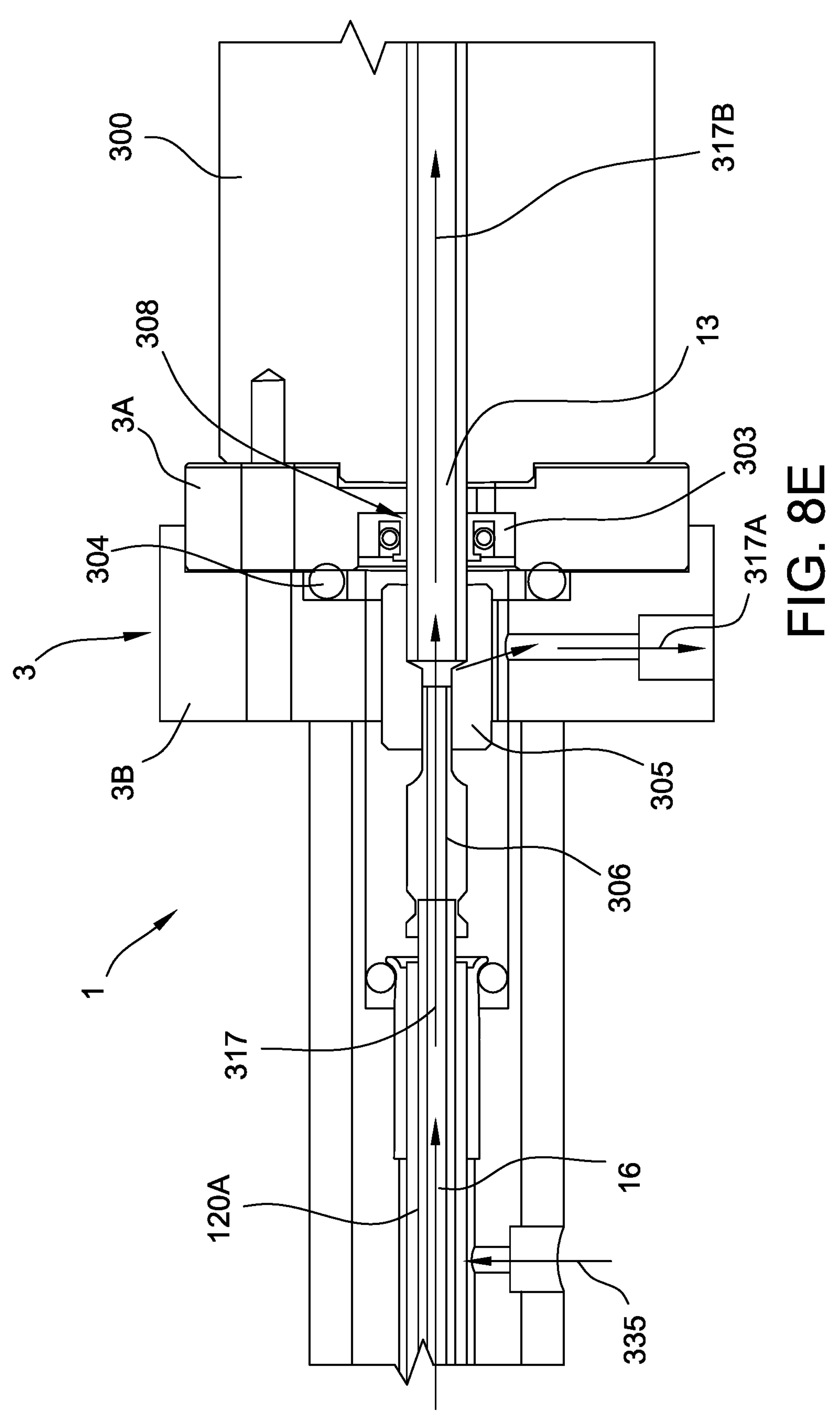
FIG. 8E is a schematic side sectional view of the motor assembly shown in FIGS. 8A-8D.
Figure 8F:
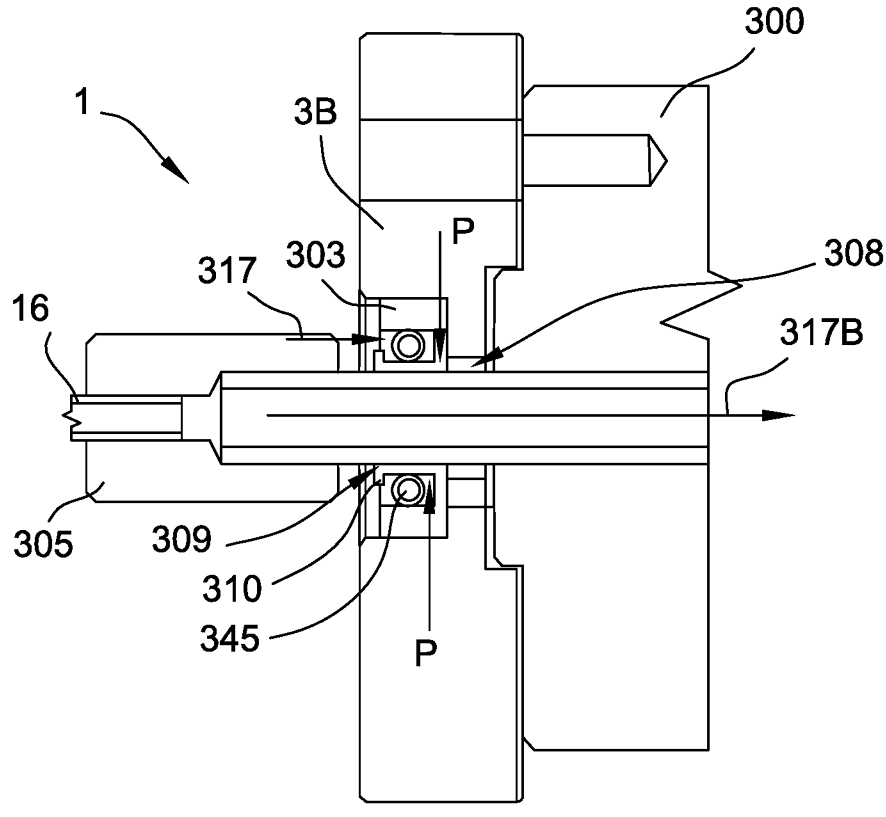
FIG. 8F is a magnified schematic side sectional view of the motor assembly shown in FIG. 8E.

FIG. 8E is a schematic side sectional view of the motor assembly 1 shown in FIGS. 8A-8D. FIG. 8F is a magnified schematic side sectional view of the motor assembly shown in FIG. 8E. As explained above, the shaft assembly 302 may extend from the motor 300 into the chamber of the flow diverter 3 through the opening 309 in the seal 303. The shaft assembly 302 (which may comprise the drive shaft 16 and the motor output shaft 13) may rotate relative to the proximal flow diverter portion 3B and the seal 303.

As shown in FIG. 8F, the seal 303 can comprise a lip sea 1 having a flange 310 which extends towards and contacts the outer periphery 308 of the shaft assembly 302 (e.g., the output shaft 13 in some embodiments). The seal 303 can be disposed about the shaft assembly 302 and can be biased radially inward to bear against the outer periphery 308 of the shaft assembly 302 to enhance the fluid sealing effect of the seal 303. For example, a biasing member 345 (e.g., a spring or other biasing member such as a canted coil spring) may be disposed in the seal 303 to cause the flange 310 to bear against the outer periphery 308 of the shaft assembly 302. In various embodiments, the seal has a cupped or canted shape. In some embodiments, the flange 310 can also define a recess into which some fluid being conveyed with the returning fluid pathway 317 can flow. The axial fluid flow component of the fluid that is conveyed in the returning fluid pathway 317 (i.e., the component of the fluid which flows generally parallel to the shaft assembly 302) can press against the flange 310 to convert the axial fluid forces (i.e., the force of the proximally-flowing fluid along a direction parallel to the shaft assembly 302) to radially inward pressure P to further bear against the outer periphery 308 of the shaft assembly 302.

In addition, in some embodiments, it can be advantageous to electrically separate or isolate the shaft assembly from the patient, for example, to reduce the risk of electrical shock from the motor. In such embodiments, an insulating coating can be provided over part or all of the shaft assembly 302 to electrically insulate the shaft assembly 302. For example, in some embodiments, a shaft assembly including the output shaft 13 can be coated in an insulating material. In some embodiments, a shaft assembly including the drive shaft 16 can be coated in an insulating material. In some embodiments, a shaft assembly including the drive shaft 16 and the output shaft 13 can be coated in an insulating material. The insulating material which coats the shaft assembly 302 can comprise any suitable insulator, such as polyimide.

Figure 8G:
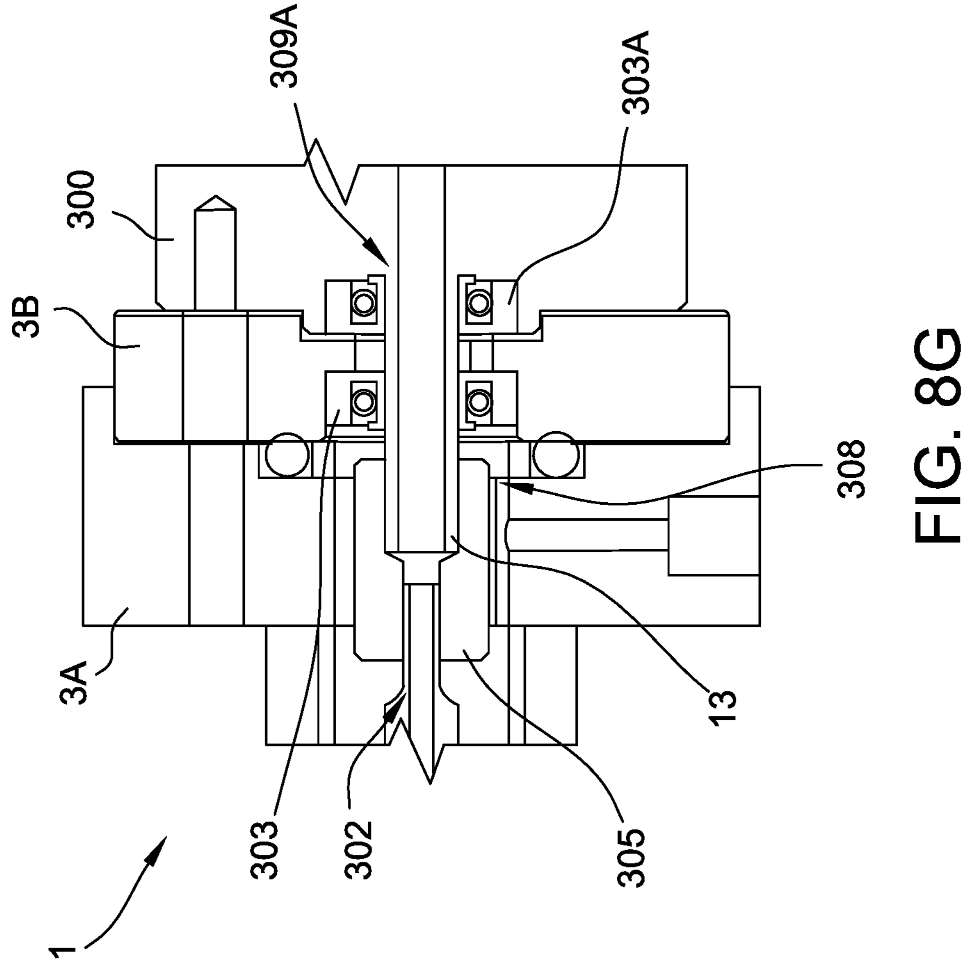
FIG. 8G is a schematic side sectional view of the seal shown in FIGS. 8A-8F.

FIG. 8G is a schematic side sectional view of the seal 303 shown in FIGS. 8A-8F. Unlike the arrangement shown in FIGS. 8A-8F, in FIG. 8G, a second seal 303A (which may be similar to the seal 303) may be disposed adjacent and proximal the proximal flow diverter portion 3B, which may act as a barrier between the motor 300 and the chamber (which may be defined by the flow diverter in some arrangements). The second seal 303A may also include an opening 309A through which a portion of the shaft assembly 302 may extend. The second seal 303A may be positioned between the flow diverter portion 3B and the motor 300. As shown, the seal 303 may be disposed adjacent and distal the proximal flow diverter portion 3B. The second seal 303A may be positioned between the flow diverter portion 3B and a distal portion of the catheter body 120A. In various arrangements, the proximal flow diverter portion 3B can act as a fluid barrier between the motor assembly 1 and a majority of the proximally-flowing fluid. Although the second seal 303A is illustrated in FIG. 8G, in various arrangements, the second seal 303A may not be provided. Thus, in FIG. 8G, the seal 303 may be disposed in the chamber of the flow diverter 3

(or other suitable structure which defines a chamber), and the second seal 303A may be disposed outside the chamber of the flow diverter 3. As explained above, the shaft assembly 302 may extend from the motor 300 into the chamber of the flow diverter 3 through the opening 309 in the seal 303. The shaft assembly 302 (which may comprise the drive shaft 16 and the motor output shaft 13) may rotate relative to the proximal flow diverter portion 3B and the seals 303, 303A.

Figure 9A:
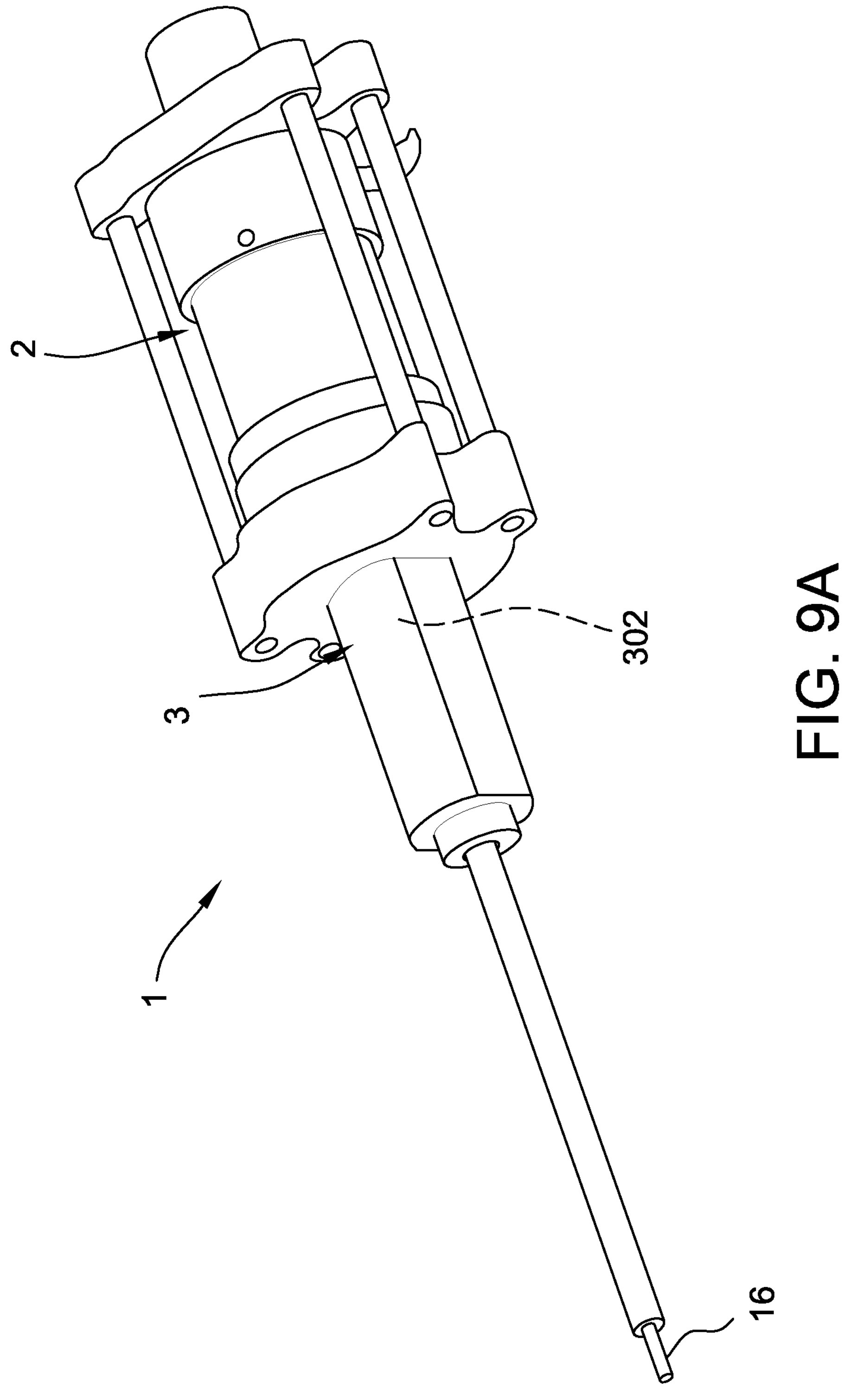
FIG. 9A is a schematic perspective view of a motor assembly, according to another embodiment.
Figure 9B:
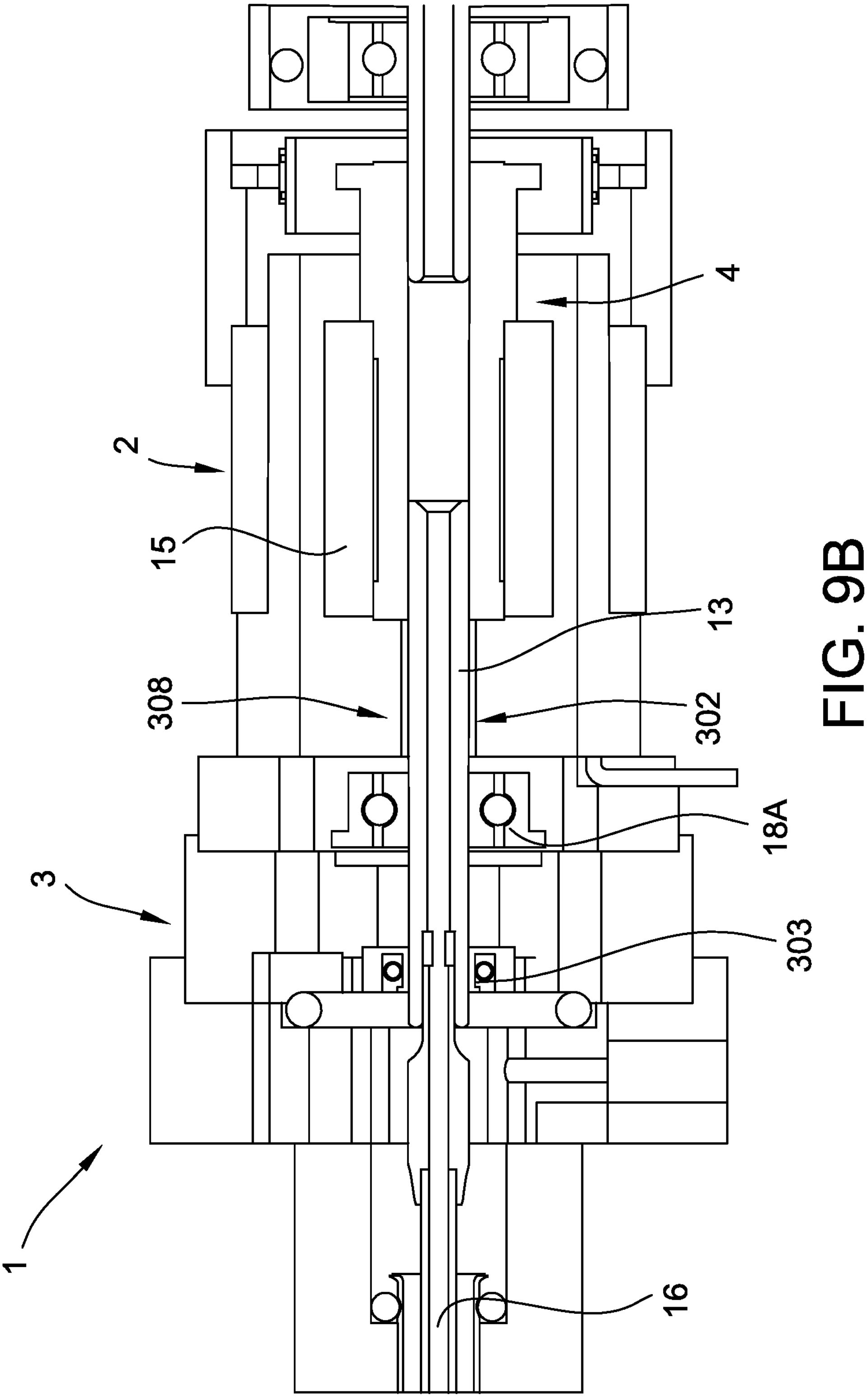
FIG. 9B is a schematic side cross-sectional view of the motor assembly of FIG. 9A.

FIGS. 9A-9B illustrate another embodiment of a motor assembly 1 with a seal 303 that prevents or impedes proximally-flowing fluid from entering the motor assembly 1 at least about an outer periphery 308 of a shaft assembly 302. In the embodiment of FIGS. 9A-9B, the motor assembly 1 is similar to the motor assembly 1 shown and described above in connection with FIGS. 2-7, except as noted herein. For example, the motor assembly of FIGS. 9A-9B can comprise a rotor 15 disposed inside a rotor chamber 4. A stator assembly 2 can be disposed outside the rotor chamber 4 about the rotor 15 and rotor chamber 4. As explained above, the windings of the stator assembly 2 can be energized to cause the rotor 15 to rotate. Rotation of the rotor 15 can cause the output shaft 13 to impart rotation to the drive shaft 16 and the impeller at the distal portion of the system. Moreover, a flow diverter 3 can be disposed distal the motor assembly 1. As explained above, the flow diverter 3 can route fluid distally to the impeller assembly and proximally to a waste reservoir. In the illustrated embodiment, the rotor 15, rotor chamber 4, and stator assembly 2 may be disposed proximal and outside the flow diverter 3.

Unlike the embodiments of FIGS. 2-7, all or a portion of the fluid flowing proximally through the catheter body 120A may be shunted around the motor assembly 1, and the motor assembly 1 can be sealed such that little or no fluid enters the motor assembly 1, e.g., little or no fluid enters the rotor chamber 4. For example, as with the embodiment of FIGS. 8A-8G, a seal 303 can be provided between the rotor chamber 4 and the flow diverter 3. The seal 303 may act as a barrier between the rotor chamber 4 and the proximally-flowing fluid. In various embodiments, the pump system is configured to selectively shunt fluid around the motor assembly. The seal 303 used in connection with FIGS. 9A-9B can be similar to the seals 303, 303A described in relation to FIGS. 8A-8G. As explained above, the seal 303 can be disposed about the shaft assembly 302 and can be biased radially inward to bear against the outer periphery 308 of the shaft assembly 302 to enhance the fluid sealing effect of the seal 303. In addition, although one seal 303 is illustrated in FIG. 9B, it should be appreciated that a second seal (such as seal 303A) can be disposed opposite the barrier, e.g., on the distal side of the barrier defined by the flow diverter 3.

Figure 10A:
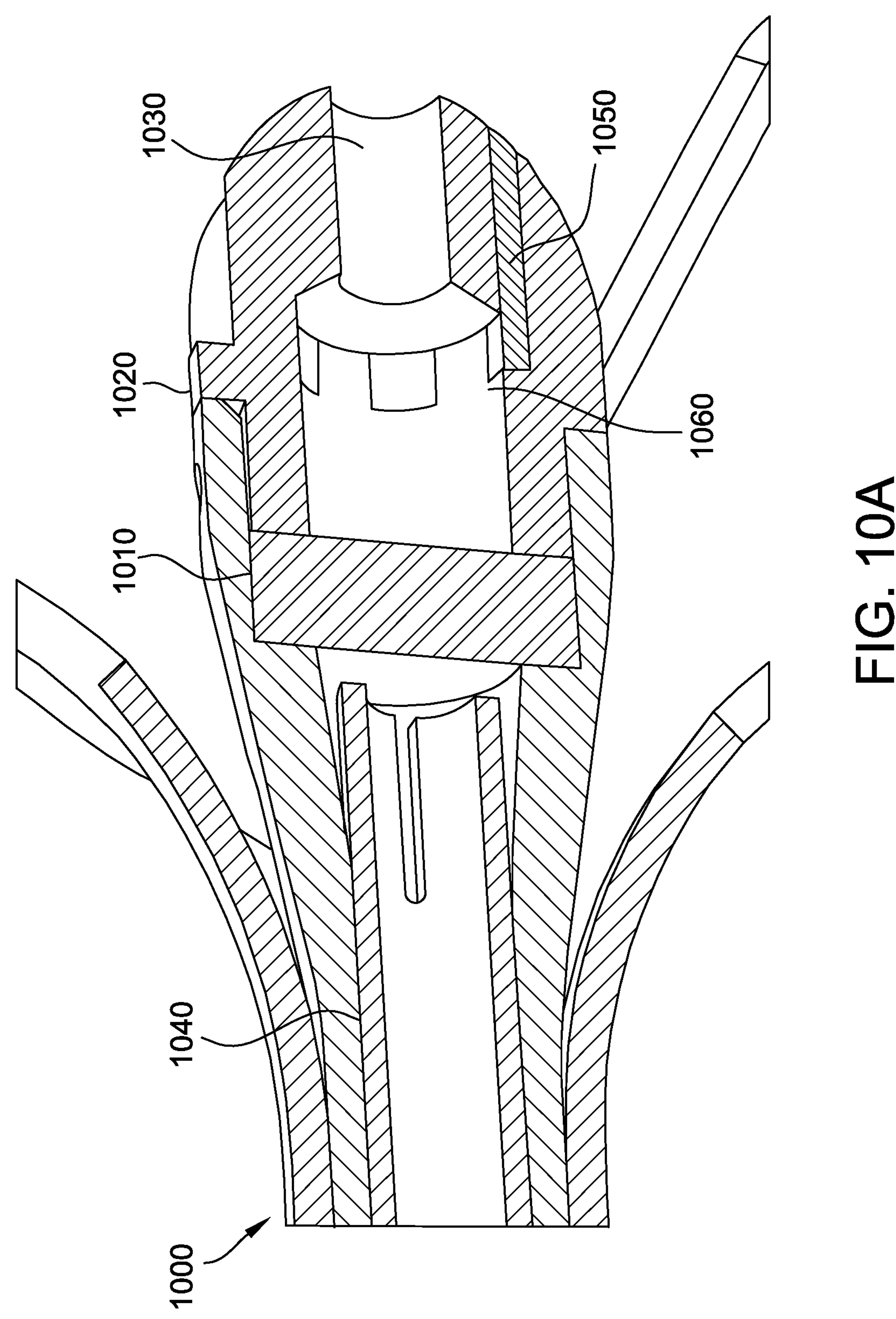
FIG. 10A illustrates a cross-sectional view of a tip of a catheter assembly according to an example.

FIG. 10A illustrates a cross-sectional view of a catheter pump 1000 according to an example. The catheter pump 1000 may be similar to the catheter pump 100A shown and described above. As indicated above, unwanted fluids, such as blood, may enter the catheter pump 1000 as the catheter pump 1000 is inserted into the body while the catheter pump is operational or otherwise spinning. In order to prevent unwanted fluid from entering the catheter pump 1000, a distal end of the catheter pump 1000 may include a seal 1010. The seal 1010 may be disposed or otherwise provided within an impeller tip 1020 of the catheter pump 1000.

In some examples, a guidewire (e.g., guidewire 235 (FIG. 1C)) may extend through the catheter pump 1000, including the seal 1010, and out of a distal end 1030 of the impeller tip 1020. In an example, the seal 1010 is comprised of a plastic or other malleable material. Thus, when the guidewire is ultimately removed, the seal 1010 closes to prevent blood or other unwanted fluids from entering a catheter tube 1040. As explained above, the catheter tube 1040 may extend through or otherwise be integrated with an impeller shaft. However, the seal 1010 may not fully close once the guidewire is removed. As a result, blood may flow through the distal end 1030 of the impeller tip 1020 and into the catheter tube 1040 and/or around an impeller shaft (e.g., impeller shaft 1110 (FIG. 11)).

In order to prevent the above, the impeller tip 1020 may include one or more features 1050 that cause the impeller tip 1020 to act as a centrifugal pump. For example, as the catheter pump 1000 is inserted into the body while running or otherwise operational, the impeller (e.g., impeller 1070 FIG. 10B) or other assembly within or otherwise associated with the catheter pump 1000 rotates thereby causing the impeller tip 1020 to rotate or spin. The impeller tip 1020 may rotate or spin in a clockwise or counterclockwise rotation.

As the impeller tip 1020 rotates, the one or more features 1050 cause blood and/or other fluids to be expelled from an inner volume 1060 defined by the impeller tip 1020. Additionally, the one or more features 1050 help create a low-pressure area at or near a distal surface of the seal 1010 within the inner volume 1060 of the impeller tip 1020. The low-pressure area enables fluids to be expelled from the inner volume 1060 of the impeller tip 1020 via the one or more features 1050.

The low-pressure area may also pull fluids (e.g., saline) from the catheter tube 1040 into the inner volume 1060. As the impeller tip 1020 spins, the saline, along with the blood, may be expelled from the inner volume 1060 via the one or more features 1050.

The one or more features 1050 may include bores, holes, cross-holes, ramps and the like that are formed or otherwise provided in the impeller tip 1020. In an example, the one or more features 1050 have a diameter of one millimeter or less. In other examples, the one or more features 1050 have a diameter of more than 1 millimeter. The one or more features may be drilled into the impeller tip 1020. In another example, the one or more features 1050 may be molded within the impeller tip 1020. Although specific examples are given, the one or more features 1050 may have any shape and/or geometry.

Figure 10B:
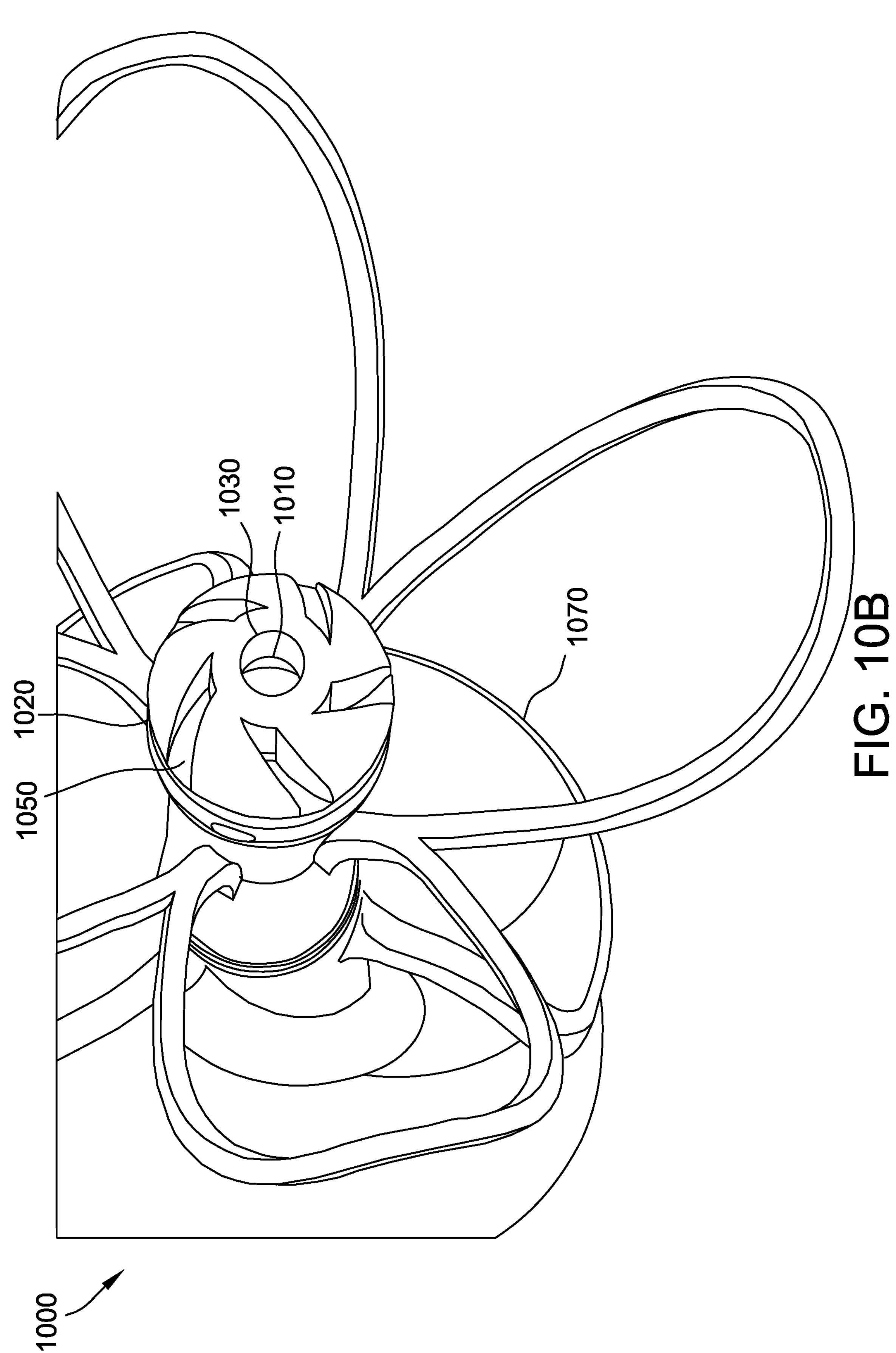
FIG. 10B illustrates a perspective view of the tip of the catheter assembly of FIG. 10A according to an example.

FIG. 10B illustrates a perspective view of the impeller tip 1020 of the catheter pump 1000 and the one or more features 1050. As shown in FIG. 10B, the impeller tip 1020 may be coupled to or otherwise associated with an impeller 1070. The impeller 1070 may be similar to the impellers shown and described above.

As also shown in FIG. 10B the one or more features 1050 are arranged in a pinwheel fashion. For example, each of the one or more features 1050 has a center hole that opens within the inner volume 1060 of the impeller tip 1020 and extends toward an outer surface of the impeller tip 1020. In an example, each of the one or more features 1050 may slope upward and/or taper from the inner volume 1060 to the outer surface of the tip 1020. Additionally, each of the one or more feature 1050 may curve or otherwise have an angle that facilitates the expulsion of fluid from the inner chamber 1060.

Although FIG. 10B illustrates the tip 1020 as having five features 1050 with specific geometries, any number of features 1050 may be used. Likewise, the geometry and/or placement of the features 1050 may vary.

Figure 11:
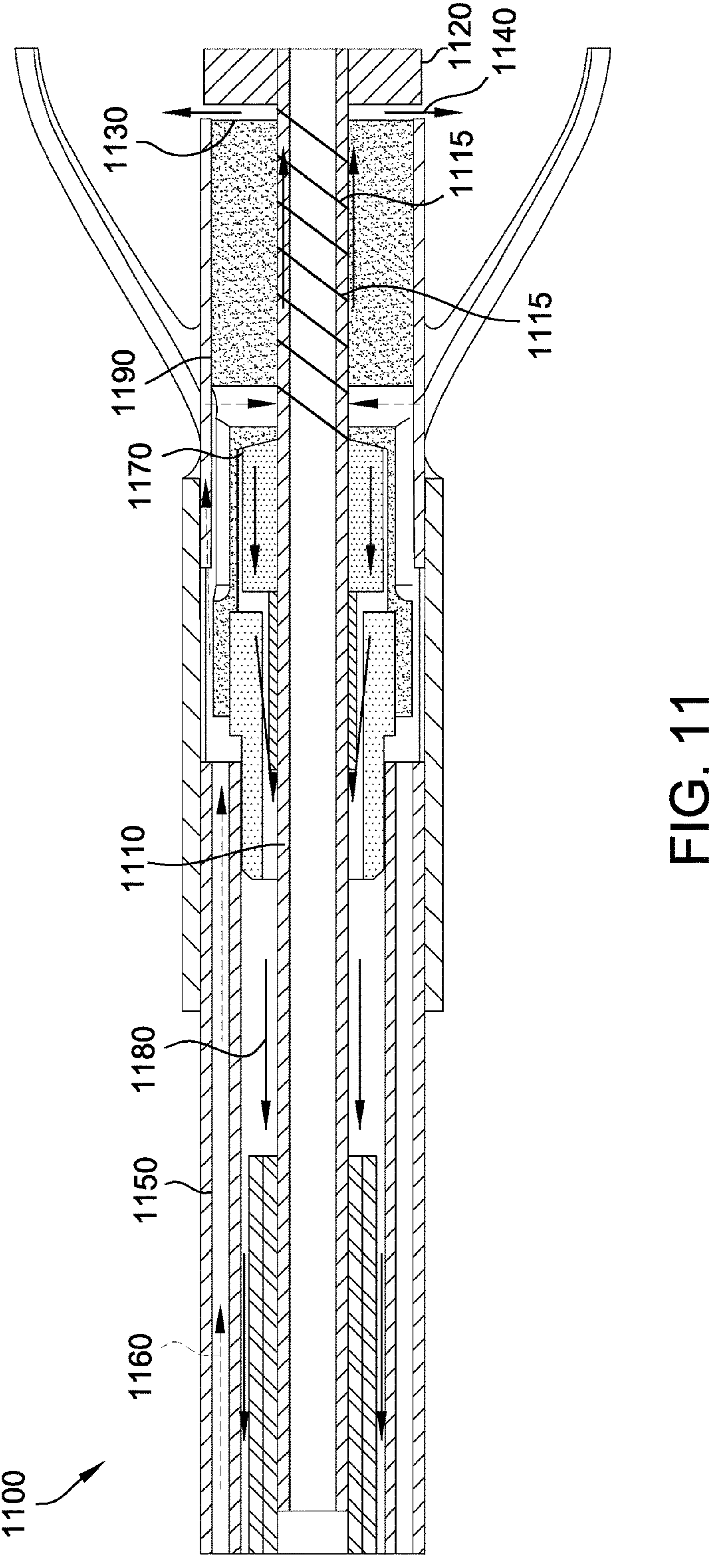
FIG. 11 illustrates a cross-sectional view of a catheter pump in which one or more grooves or channels are provided on an impeller shaft according to an example.

FIG. 11 illustrates a cross-sectional view of a catheter pump 1100 according to an example. The catheter pump 1100 may be similar to the catheter pump 100A shown and described above. The example shown in FIG. 11 illustrates how unwanted fluids may be prevented from contacting or otherwise interfering with an impeller shaft 1110 of the catheter pump 1100. Additionally, unwanted fluids may be expelled from a portion of the catheter pump 1100 using the examples described with respect to FIG. 11.

In some examples, the catheter pump 1100 may enable a fluid, such as saline, to be pumped through an inner sheath lumen 1150 and into a bearing housing 1190 of the catheter pump 1100. In this example, the fluid moves within the inner sheath lumen 1150 in the direction of arrow 1160. Likewise, fluid may be pumped into or otherwise provided around a thrust bearing 1170 in the direction of arrows 1180. The fluid may be used as a lubricant for various components of the catheter pump 1100.

As shown in FIG. 11, the catheter pump 1100 also includes an impeller shaft 1110 coupled to an impeller 1120. The impeller shaft 1110 may extend through the thrust bearing 1170 and the bearing housing 1190. In an example, the impeller shaft 1110 rotates about an axis while the bearing housing 1190 is stationary. Rotation of the impeller shaft 1110 causes the impeller 1120 to rotate.

As the catheter pump 1100 is inserted into the body while running or otherwise operational, blood or other fluids may flow along an outer surface of the impeller 1120 (e.g., from a distal end of the impeller 1120) and into a gap 1130 between the impeller 1120 and the bearing housing 1190. In addition, blood or other unwanted fluids may penetrate through a seal of the catheter pump 1100 such as described above with respect to FIG. 10A.

In order to prevent the unwanted fluids from contacting the impeller shaft 1110, various channels or grooves 1115 may be formed or otherwise provided on an outer surface of the impeller shaft 1110. In an example, the grooves 1115 are helically arranged on the outer surface of the impeller shaft 1110. For example, the grooves 1115 may be etched or brushed on the outer surface of the impeller shaft 1110.

As the impeller shaft 1110 rotates, the grooves 1115 may move the fluid from a first location along the impeller shaft 1110 (e.g., near the thrust bearing 1170) toward a second location along the impeller shaft (e.g., toward the gap 1130). As the grooves 1115 move the fluid toward and/or through the gap 1130, the fluid may be expelled from the gap 1130 in the direction of arrows 1140. Movement of the fluid in this manner may also cause blood or other unwanted fluids to be expelled from the gap 1130. In another example, the pressure caused by movement of the fluid along the grooves 1115 may prevent unwanted fluids from entering the gap 1130 and/or contacting the impeller shaft 1110.

Figure 12A:
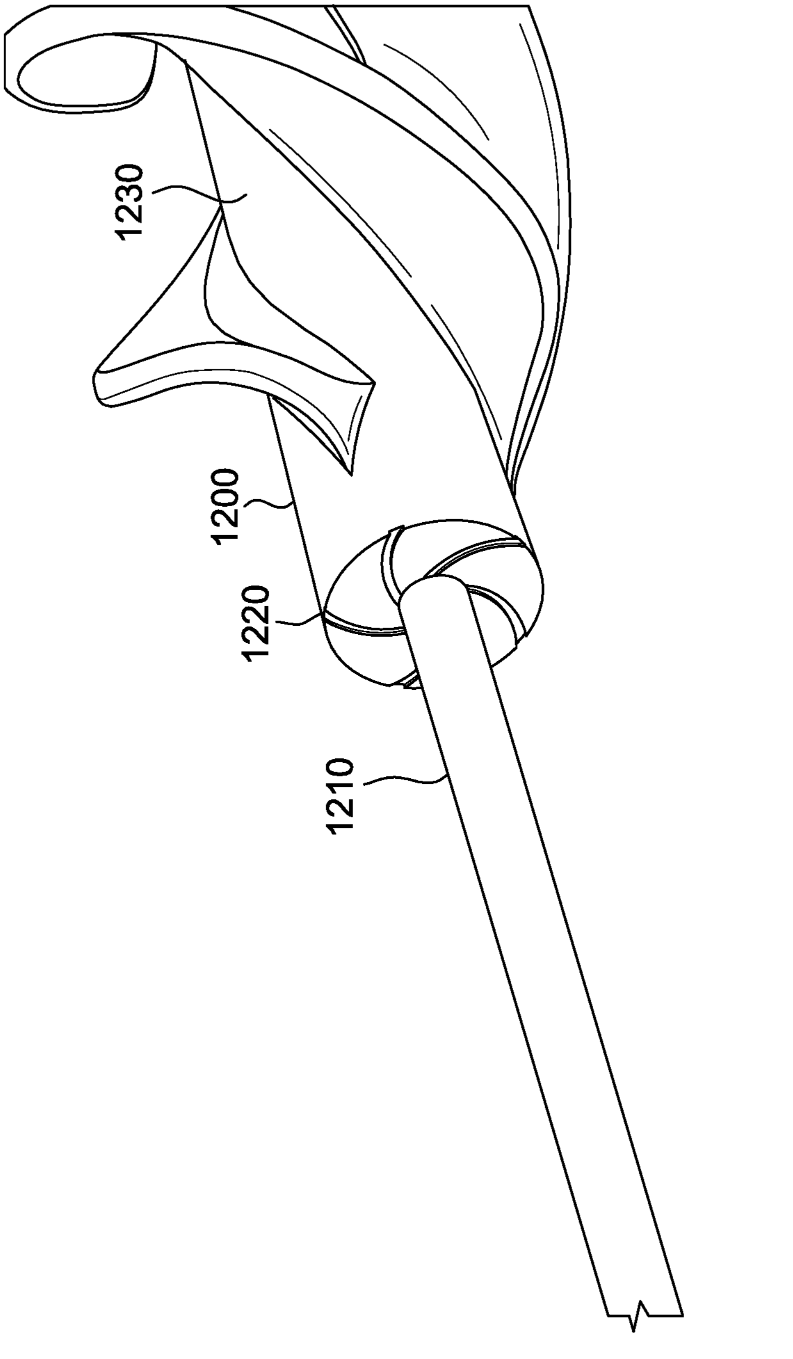
FIG. 12A illustrates an example surface feature provided on an impeller of a catheter pump to expel unwanted fluid according to an example.

FIG. 12A illustrates an example surface feature 1220 provided on an impeller 1200 of a catheter pump to expel unwanted fluid according to an example. In an example, the impeller may be similar to the impeller 1120 described above with respect to FIG. 10A-FIG. 11 and/or the other impellers described herein.

In the example shown in FIG. 12A, the impeller 1200 is coupled to an impeller shaft 1210. The impeller shaft 1210 may be similar to the impeller shaft described above with respect to FIG. 10A-FIG. 11 and/or the other impeller shafts described herein. A surface feature 1220 may be defined by the impeller 1220 or may otherwise be provided on a proximal (or distal) surface of the impeller 1200. The surface feature 1220 may include a number of channels or grooves that enable the proximal surface on which the surface features 1220 are provided to act as a centrifugal pump. In an example, the proximal surface on which the surface feature 1220 is defined may be between the impeller 1200 and a bearing housing (e.g., bearing housing 1190 (FIG. 11)).

As explained above with respect to FIG. 11, a gap (e.g., gap 1130) may be disposed between the proximal end of the impeller 1200 and the bearing housing. Accordingly, blood or other unwanted fluids may flow along an outer surface 1230 of the impeller 1200 and onto the proximal surface. Should that occur, the surface feature 1220 on the proximal end of the impeller may act as a centrifugal pump thereby causing the blood or unwanted fluid to be expelled from the surface. As discussed above, the surface feature 1220 may be a channel or groove. The surface feature 1220 receives the unwanted fluid and expels the fluid from the gap and/or the proximal surface of the impeller 1200. The surface feature 1220 may also be used to expel saline from the gap such as described above with respect to FIG. 11.

Figure 12B:
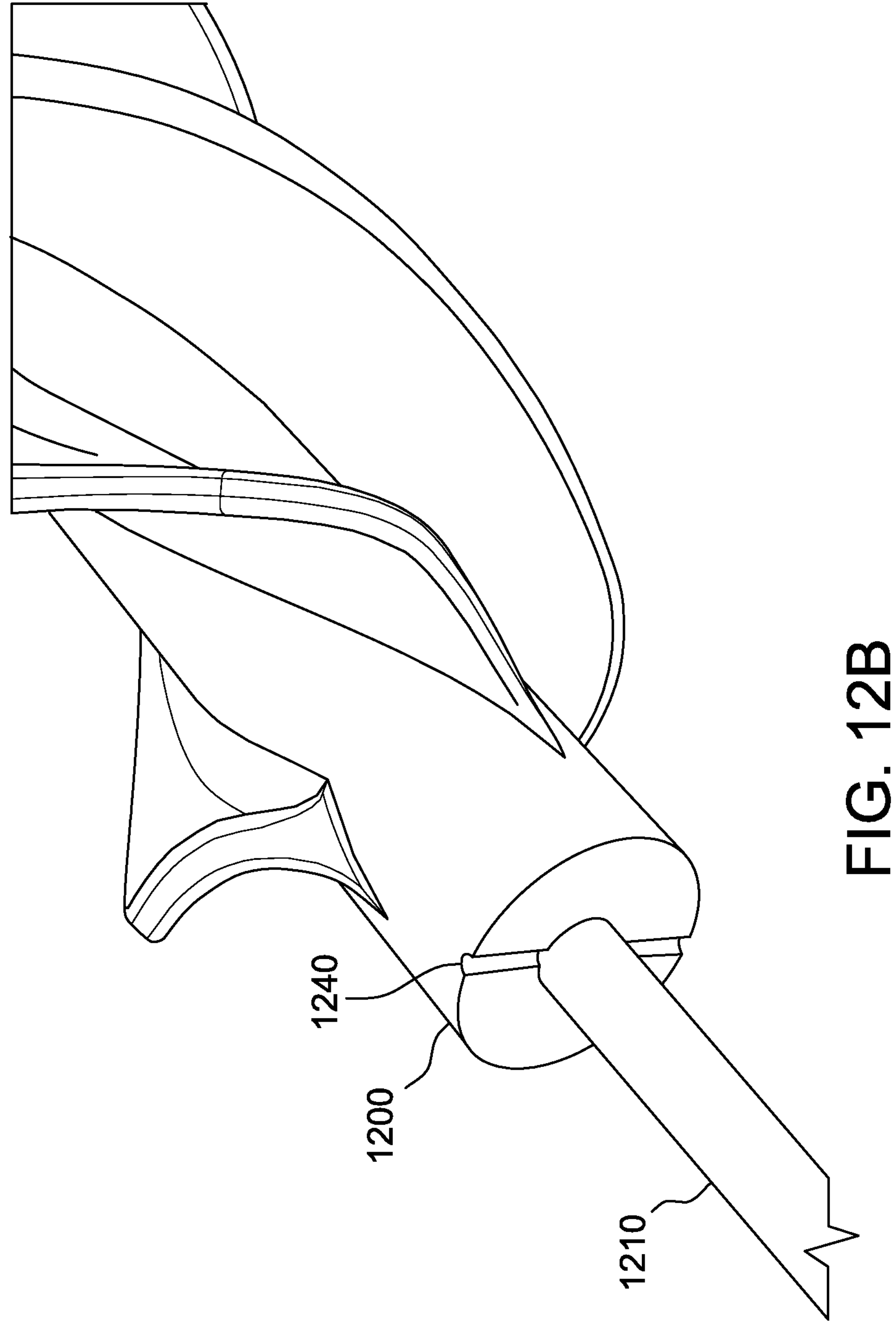
FIG. 12B illustrates another example of a surface feature provided on an impeller of a catheter pump to expel unwanted fluid according to an example.

Although FIG. 12A illustrates a particular number and shape/geometry of the surface feature 1220, the impeller 1200 may have any number of surface features in a number of different geometries. For example, FIG. 12B illustrates another example of a surface feature 1240 provided on an impeller 1200 of a catheter pump to expel fluids according to an example. The surface feature 1240 acts in a similar manner as the surface feature 1220 described above.

Although the embodiments disclosed herein have been described with reference to particular embodiments, it is to be understood that these embodiments are merely illustrative of the principles and applications of the present inventions. It is therefore to be understood that numerous modifications can be made to the illustrative embodiments and that other arrangements can be devised without departing from the spirit and scope of the present inventions as defined by the appended claims. Thus, it is intended that the present application cover the modifications and variations of these embodiments and their equivalents.

What is claimed is:

1. A catheter pump system, comprising:
an impeller defining an open inner volume; and
one or more channels extending from an outer surface of the impeller to the inner volume, wherein movement of the impeller expels a radial flow of fluid through the one or more channels from the open inner volume.

2. The catheter pump system of claim 1, wherein the impeller comprises an impeller tip, wherein the catheter pump system further comprises a seal provided within the impeller tip.

3. The catheter pump system of claim 2, wherein the seal has a distal surface and the one or more channels create a low-pressure area at the distal surface of the seal.

4. The catheter pump system of claim 1, wherein the one or more channels acts as a centrifugal pump.

5. The catheter pump system of claim 1, wherein the one or more channels comprise one or more cross-holes.

6. The catheter pump system of claim 1, further comprising one or more grooves disposed on an impeller shaft of the impeller.

7. The catheter pump system of claim 6, wherein the one or more grooves are helically arranged on the impeller shaft of the impeller.

8. The catheter pump system of claim 6, wherein the one or more grooves move a fluid from a proximal location associated with the impeller shaft to a distal location associated with the impeller shaft.

9. The catheter pump system of claim 6, wherein the one or more grooves assist with the expulsion of a fluid from a gap between the impeller and a bearing housing of the catheter pump system.

10. The catheter pump system of claim 1, further comprising a surface feature provided on a proximal surface of the impeller.

11. The catheter pump system of claim 10, wherein the surface feature is a channel.

12. The catheter pump system of claim 10, wherein the surface feature acts as a centrifugal pump to expel a fluid from a gap between the impeller and a bearing housing of the catheter pump system.

13. A catheter pump system, comprising:

an impeller defining an inner volume and a plurality of features, wherein each of the plurality of features defines a channel between the inner volume and a surface of the impeller; and an impeller shaft coupled to the impeller, the impeller shaft comprising one or more fluid directing passages, wherein each of the one or more fluid directing passages and each of the plurality of features act to expel a fluid from the inner volume of the impeller in response to movement of the impeller.

14. The catheter pump system of claim 13, wherein movement of the impeller further creates a low-pressure region within the inner volume of the impeller.

15. The catheter pump system of claim 14, wherein movement of the impeller expels the fluid through the channel to the surface of the impeller.

16. The catheter pump system of claim 14, wherein the one or more fluid directing passages expels the fluid from a gap between the impeller and a bearing housing of the catheter pump system.

17. The catheter pump system of claim 14, further comprising a surface feature provided on a proximal surface of the impeller.

18. The catheter pump system of claim 17, wherein the surface feature acts as a centrifugal pump to expel a fluid from a gap between the impeller and a bearing housing of the catheter pump system.

19. The catheter pump system of claim 14, wherein the plurality of channels define a slope from the inner volume to the surface portion of the impeller tip.

20. A method, comprising:

causing a movement an impeller of a catheter pump system; and in response to the movement of the impeller, expelling a fluid from an open inner volume defined by the impeller, wherein the fluid is expelled from the open inner volume via a plurality of channels, each of the plurality of channels defining a channel path that extends from the open inner volume to an outer surface of the impeller.

21. The method of claim 20, further comprising:

displacing fluid from a first portion of the catheter pump system using a surface feature provided on a proximal surface of the impeller; and displacing fluid from a second portion of the catheter pump system using one or more fluid directing components defined by the impeller.

22. The catheter pump system of claim 1, wherein movement of the impeller further creates a low-pressure region within the inner volume of the impeller.

* * * * *